United States Patent
Kai

(10) Patent No.: US 8,183,060 B2
(45) Date of Patent: May 22, 2012

(54) LUMINESCENT POLYMER AND USE THEREOF IN BIOASSAY

(75) Inventor: Masaaki Kai, Nagasaki (JP)

(73) Assignees: Daiichi Pure Chemicals Co., Ltd., Chuo-Ku, Tokyo (JP); Kai Masaaki, Nagasaki-Shi, Nagasaki (JP)

( * ) Notice: Subject to any disclaimer, the term of this patent is extended or adjusted under 35 U.S.C. 154(b) by 949 days.

(21) Appl. No.: 10/490,182

(22) PCT Filed: Sep. 19, 2002

(86) PCT No.: PCT/JP02/09649
§ 371 (c)(1),
(2), (4) Date: Sep. 13, 2004

(87) PCT Pub. No.: WO03/031974
PCT Pub. Date: Apr. 17, 2003

(65) Prior Publication Data
US 2005/0019573 A1    Jan. 27, 2005

(30) Foreign Application Priority Data
Sep. 19, 2001 (JP) .................................. 2001-285502

(51) Int. Cl.
G01N 33/533 (2006.01)
G01N 33/548 (2006.01)
G01N 21/76 (2006.01)
(52) U.S. Cl. .......... 436/546; 436/548; 436/172; 435/7.5
(58) Field of Classification Search .................... 435/7.1, 435/7.92, 7.93; 436/56, 529, 532, 543, 546; 530/402
See application file for complete search history.

(56) References Cited

U.S. PATENT DOCUMENTS

| 4,363,759 | A  | * | 12/1982 | Boguslaski et al. .......... 530/303 |
| 5,019,521 | A  |   | 5/1991  | Krupey |
| 5,420,016 | A  | * | 5/1995  | Boguslaski et al. ............ 435/12 |
| 5,707,877 | A  | * | 1/1998  | Siiman et al. ................. 436/518 |
| 6,030,846 | A  | * | 2/2000  | Simons et al. ................ 436/537 |
| 6,627,460 | B1 | * | 9/2003  | Lihme et al. .................. 436/529 |
| 2003/0054413 | A1 | * | 3/2003 | Kumaraswamy et al. ..... 435/7.5 |

FOREIGN PATENT DOCUMENTS
EP    0640836 A2    3/1995
(Continued)

OTHER PUBLICATIONS

Novikova et al. Persistent neuronal labeling by retrograde fluorescent tracers: a comparison between Fast Blue, Fluoro-gold and various dextran conjugates. Journal of Neuroscience Methods, 1997, vol. 74, pp. 9-15.*

(Continued)

*Primary Examiner* — Shafiqul Haq
(74) *Attorney, Agent, or Firm* — Knobbe Martens Olson & Bear LLP

(57) ABSTRACT

It is an object of the present invention to provide a luminescent polymer that is useful as a luminescent signal probe for labeling and detecting a target substance at high sensitivity in bioassay, and to provide the application of said luminescent polymer to bioassay.

The luminescent polymer of the present invention comprises at least one biotin covalently attached to a polymer that includes monosaccharide or amino acid as a constituent monomer covalently attached to a luminescent substance. Preferably, two or more biotins are attached. Examples of the above-mentioned luminescent substance include cyanoisoindoles, luminols, and acridinium esters, and examples of the polymer include polysaccharides, polyamino acids, peptides, polypeptides, and proteins.

13 Claims, 1 Drawing Sheet

FOREIGN PATENT DOCUMENTS

| | | |
|---|---|---|
| JP | 58-061468 | 4/1983 |
| JP | 58-137759 | 8/1983 |
| JP | 58-137760 | 8/1983 |
| JP | 02-102203 | 4/1990 |
| JP | 02-502122 A | 7/1990 |
| JP | 06-158039 A | 6/1994 |
| JP | 07-63758 A | 3/1995 |
| JP | 07-330838 | 12/1995 |
| JP | 08-113611 | 5/1996 |
| JP | 09-100415 A | 4/1997 |
| JP | 09-302033 | 11/1997 |
| JP | 2001-249131 A | 9/2001 |
| WO | WO 88/05538 | 7/1988 |
| WO | WO 90/00252 A1 | 1/1990 |
| WO | WO 98/31732 A2 | 7/1998 |
| WO | WO 00/07019 | 2/2000 |

OTHER PUBLICATIONS

Gee et al. Caged Q-rhodamine dextran: A new photoactivated fluorescent tracer. Bioorganic and Medicinal Chemistry Letters, 2001, vol. 11, pp. 2181-2183.*

Pinkel et al. Cytogenetic analysis using quantitative, high-sensitivity, fluorescence hybridization. PNAS 1986, vol. 83, pp. 2934-2938.*

Handbook of Fluorescent Probes and Research Products, Section 14.5, Molecular Probes, Inc, 2001.*

Handbook of Fluorescent Probes and Research Products, Section 4.3, Molecular Probes, Inc. 2001.*

Beck, Stephan and Koster, Hubert, *Analytical Chemistry*, vol. 62, No. 21: pp. 2258-2270, Nov. 1, 1990, "Applications of Dioxetane Chemiluminescent Probes to Molecular Biology."

Renotte, R., et al., *Luminescence*, vol. 15: pp. 311-320, 2000, "High stability and high efficiency chemiluminescent acridinium compounds obtained from 9-acridine carboxylic esters of hydroxamic and sulphohydroxamic acids."

C. Dodeigne, et al., *Talanta*, vol. 51: pp. 415-439, 2000, "Chemiluminescence as diagnostic tool. A review."

Nikiforov, T.T. et al. 2001 "New applications of flurorescence polarization for enzyme assays and in genomics" *Proc of the The International Society for Optical Engineering (SPIE)* 4255:94-105.

* cited by examiner

US 8,183,060 B2

LUMINESCENT POLYMER AND USE THEREOF IN BIOASSAY

This application is the U.S. National Phase under 35 U.S.C. §371 of International Application PCT/JP02/09649, filed on Sep. 19, 2002, which claims priority of Japanese Patent Application No. 2001-285502, filed on Sep. 19, 2001. The International Application was published under PCT Article 21(2) in a language other than English.

TECHNICAL FIELD

This invention relates to a luminescent polymer that is useful for detecting a target substance at high sensitivity, and also to a method for manufacturing the luminescent polymer. This invention also relates to the applications of the luminescent polymer as a luminescent signal probe and a luminescent reagent, and to bioassay methods in which the luminescent polymer is used as a signal probe for a target substance.

BACKGROUND ART

Fluorescent and chemiluminescent signal probes have recently come into widespread use, in place of conventional radioactive signal probes for the detection and quantification of nucleic acids, sequence analysis, hybridization assays, immunological measurements, and so forth. In general, the optical detection method is safer and simpler than detection methods involving the use of radiation, and its spectroscopic devices have be advanced in recent years, for good selectivity and sensitivity comparable to that of radiochemical methods.

However, there remains a great need for higher sensitivity of detection. For instance, if molecule-countable level of DNA or RNA could ultimately be detected, it would be an easy matter to analyze the genomic DNA or RNA in a single cell. Also, there has been a need for the development of an excellent signal probe and its technology for easily and rapidly detecting differences in the molecular level of nucleic acids between normal and abnormal cells and in the cells of tissues or organs.

With efforts to increase the sensitivity of detection, various studies have being conducted on the research points of labeling reagents, signal probe and detector device.

The genomic DNA in a single cell can be detected by conventional fluorescent-labeling or dye-staining technique, when the nucleotides of DNA are polymerized in kilo-units or larger. However, it is extremely difficult to detect a difference of a single base in a DNA sequence (SNPS: Single Nucleotide Polymorphisms) or a difference of a few bases in a DNA sequence, even with today's fluorescent labeling technique. Thus, a sample (such as DNA) quantity at least 10 fmol is required even when using laser fluorescent dyes that are known as highly sensitive fluorescent dyes.

Also, when a fluorescent dye is used for detection, even with multiple fluorescent dyes for intensifying, quenching phenomenon may occur according to the increase of the fluorescent dyes, which may lead to the unsatisfactory detection sensitivity. Accordingly, it is no easy to detect an extremely small mutation points in a DNA sequence with fluorescent dyes.

There have also been proposed fluorescent and chemiluminescent detection methods that make use of an enzyme probe operating on the principle of amplifying the sensitivity by enzyme reaction time (Stephan Beck and Hubert Koster, Anal. Chem., 60, 2258-2270 (1990)). However, the degree of sensitivity amplification in their methods is dependent on the enzyme reaction time. If there is only a very small amount of target substance, therefore the enzyme reaction takes a long time in order to raise the sensitivity, it is difficult to obtain data rapidly, and the background noise is also amplified at the same time, which can result in inferior resolution for the detection.

In an attempt to achieve higher detection sensitivity, various luminescent detection methods have been proposed, in which a polymer comprising many fluorescent or chemiluminescent substances is used as a labeling agent. Specific examples include a method in which an acridinium compound having a plurality of acridinium rings, or a complex thereof, is used as a chemiluminescent labeling agent (Japanese Laid-Open Patent Applications H6-158039 and H9-100415); a method in which an acridan group-containing polymer having a repeating domain of acridan group joined portion [a (meth)acrylic acid (co)polymer, polyvinyl alcohol, or polyethylene glycol (meth)acrylate copolymer] is used as a chemiluminescent labeling agent (Japanese Laid-Open Patent Applications H7-330838, H8-113611, and H9-302033); and a method in which an organic polymer (such as a synthetic peptide or polyvinylphenol) bound with a plurality of luminescent substance such as luminol or lucigenin is used as a chemiluminescent labeling agent in immunoassay (Japanese Laid-Open Patent Applications S58-61468, S58-137759, and S58-137760). Also, although not aimed at highly sensitive detection, Japanese Laid-Open Patent Application H2-102203 reports that the binding of a luminescent substance such as luminol to a polyvinyl alcohol in order to increase the water solubility of the luminescent substance, and this luminescent substance is usable as a reagent for evaluating the bio-membrane permeability. However, as shown from the above-mentioned publications, there is no report that is disclosed a compound (including a polymer) comprising one or more fluorescent or chemiluminescent substances bound thereto, and also being capable of amplifying luminescent intensity by themselves mutually forming complexes sequentially, and a technique for amplification of the luminescent intensity using the said compound.

DISCLOSURE OF THE INVENTION

It is an object of the present invention to provide a luminescent polymer that can be utilized to detect a target substance at a high sensitivity in a safe and simple optical method, and a method for manufacturing the polymer. It is another object of the present invention to provide an application of the luminescent polymer as a luminescent signal probe and luminescent reagent (labeling/detection reagent). It is a further object of the present invention to provide a bioassay method for detecting a target substance at high sensitivity by utilizing this luminescent polymer as a luminescent signal probe.

As a result of diligent research for developing a luminescent signal probe for the highly sensitive detection of a target substance by an optical method, the inventors found that (1) by binding a luminescent substance to a constituent monomer (amino acid or monosaccharide) of a polymer such as a polyamino acid, a peptide, a polypeptide, a protein, or a polysaccharide, strong luminescence intensity can be obtained depending on the number of attached luminescent substances, (2) a target substance can be specifically labeled via binding with avidin or streptavidin by binding biotin to the above-mentioned luminescent polymer (so-called biotin-labeled luminescent polymer), and (3) when a compound in which two or more biotins are attached to a single molecule is used as the biotin-labeled luminescent polymer, several biotin-labeled luminescent polymers can bind cooperatively in a network structure through binding with avidin or streptavidin.

On the basis of these findings, the inventor confirmed that the luminescent intensity from the above-mentioned biotin-labeled luminescent polymer can be increased in proportion to the number of luminescent substances bound to the polymer, and that the luminescent intensity from a luminescent polymer with two or more biotins can be further amplified by making a complex of numerous biotin-labeled luminescent polymers, allowing this product to be used effectively as a high-sensitivity luminescent signal probe. In addition, the inventor confirmed that the above-mentioned biotin-labeled luminescent polymer in which a backbone polymer is water-miscible polymer such as polyamino acids, peptides, and polysaccharides, is applicable in various fields as a luminescent signal probe to measure bio-components in bioassay. The present invention was developed on the basis of these findings.

Specifically, the present invention relates to a biotin-labeled luminescent polymer given below.

I. A luminescent polymer comprising at least one biotin covalently attached to a polymer, the polymer including as a constituent monomer a monosaccharide or an amino acid covalently attached to a luminescent substance.

In this Specification, the above-mentioned luminescent polymer comprising covalently attached biotin is also referred to as a "biotin-labeled luminescent polymer."

This biotin-labeled luminescent polymer includes the following specific aspects.

I-1. A luminescent polymer comprising two or more biotins covalently attached to a polymer, the polymer including as a constituent monomer a monosaccharide or an amino acid covalently attached to a luminescent substance.

I-2. The luminescent polymer according to I or I-1, wherein the luminescent substance is a chemiluminescent substance or a fluorescent substance.

I-3. The luminescent polymer according to any of I, I-1, or I-2, wherein the luminescent substance is at least one compound selected from among cyanoisoindoles, luminols, and acridinium esters.

I-4. The luminescent polymer according to I-3, wherein the cyanoisoindoles include a compound expressed by the following formula:

[First Chemical Formula]

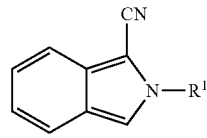

(1)

(where $R^1$ is any group).

I-5. The luminescent polymer according to I-3, wherein the luminol include a compound expressed by the following formula:

[Second Chemical Formula]

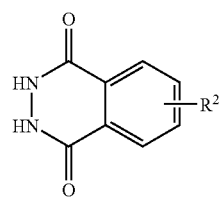

(2)

(where $R^2$ is any group).

I-6. The luminescent polymer according to I-3, wherein the acridinium ester include a compound expressed by the following formula:

[Third Chemical Formula]

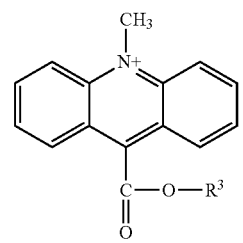

(3)

(where $R^3$ is any group).

I-7. The luminescent polymer according to any of I to I-6 above, wherein the polymer is a polyamino acid or a polysaccharide.

I-8. The luminescent polymer according to any of I to I-6 above, wherein the polymer is a polysaccharide.

I-9. The luminescent polymer according to any of I to I-8 above, wherein the polymer is dextran or pullulan.

I-10. The luminescent polymer according to any of 1 to I-9 above, wherein the luminescent polymer is water-soluble.

I-11. The luminescent polymer according to any of I to I-10 above, wherein the polymer includes a monosaccharide as a constituent monomer; at least one luminescent substance selected from the group consisting of cyanoisoindoles having a primary amino group, luminols having a primary amino group, and acridinium esters having a primary amino acid group is covalently attached through a dehydrative condensation to a ring-opened aldehyde group produced by the oxidation of the monosaccharide; and a hydrazino group (—NH—NH$_2$) of a hydrazide derivative of biotin is covalently attached to a ring-opened aldehyde of another monosaccharide.

I-12. The luminescent polymer according to I-11 above, wherein the cyanoisoindoles having a primary amino group include a compound expressed by the following formula (7):

[Fourth Chemical Formula]

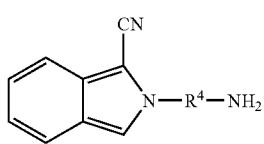

(7)

(where $R^4$ is a spacer), the luminols having a primary amino group include a compound expressed by the following formula (8):

[Fifth Chemical Formula]

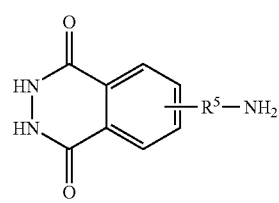

(8)

(where $R^5$ is a single bond or a spacer), the acridinium esters having a primary amino group include a compound expressed by the following formula (9):
[Sixth Chemical Formula]

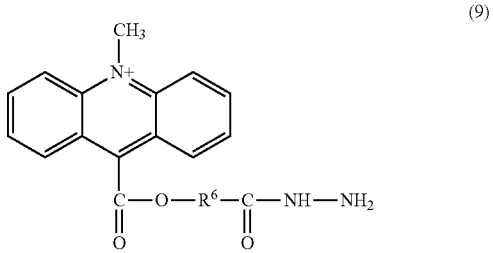

(9)

(where $R^6$ is a single bond or a spacer),
and the hydrazide derivative of biotin includes a compound expressed by the following formula:
[Seventh Chemical Formula]

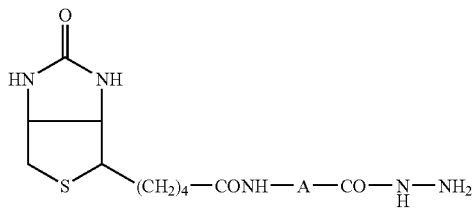

(where A is a spacer).

The present invention further relates to a method for manufacturing the above-mentioned biotin-labeled luminescent polymer, as given below.

II. A method for manufacturing the biotin-labeled luminescent polymer according any of I and I-1 to I-12 above, comprising the following steps (a) and (b):
(a) reacting at least one luminescent substance with a polymer including a monosaccharide or an amino acid as a constituent monomer and introducing the luminescent substance to the monomer; and
(b) covalently attaching biotin to the polymer including a monosaccharide or an amino acid as a constituent monomer.

Said manufacturing method includes the following aspects.

II-1. A method for manufacturing the biotin-labeled luminescent polymer according to I-11 or I-12 above, comprising the following steps (c) and (d):
(c) covalently attaching by a dehydrative condensation at least one luminescent substance selected from the group consisting of cyanoisoindoles having a primary amino group, luminols having a primary amino group, and acridinium esters having a primary amino group to a ring-opened aldehyde group in a polymer including a monosaccharide as a constituent monomer produced by oxidation of the monosaccharide; and
(d) covalently attaching a hydrazino group (—NH—NH$_2$—) of a hydrazide derivative of biotin to another such ring-opened aldehyde group produced by the oxidation of another monosaccharide of the polymer including a monosaccharide as a constituent monomer.

The above-mentioned steps (a) and (b), and (c) and (d) may be performed irrespective of order, that is, step (b) may be performed after step (a) (or step (d) may be performed after step (c)), or step (a) may be performed after step (b) (or step (c) may be performed after step (d)).

The present invention further relates to a luminescent signal probe utilizing a biotin-labeled luminescent polymer, as given below.

III. A luminescent signal probe consisting of the biotin-labeled luminescent polymer according to any of the above-mentioned I and I-1 to I-12.

This luminescent signal probe can be provided as a chemiluminescent signal probe when the luminescent substance used in the preparation of the biotin-labeled luminescent polymer is a chemiluminescent substance (when the luminescent polymer is a chemiluminescent polymer), or as a fluorescent signal probe when the luminescent substance is a fluorescent substance (when the luminescent polymer is a fluorescent polymer).

This luminescent signal probe includes the following aspects.

III-1. The luminescent signal probe according to III, which is used for labeling and detecting a target substance in bioassay.

III-2. The luminescent signal probe according to III, which is used for amplifying luminescent intensity in bioassay.

The present invention further relates to a luminescent reagent utilizing a biotin-labeled luminescent polymer, as given below.

IV. A luminescent reagent containing the biotin-labeled luminescent polymer according to any of the above-mentioned I and I-1 to I-12.

This luminescent reagent can be provided as a chemiluminescent reagent when the luminescent substance used in the preparation of the biotin-labeled luminescent polymer is a chemiluminescent substance (when the luminescent polymer is a chemiluminescent polymer), or as a fluorescent reagent when the luminescent substance is a fluorescent substance (when the luminescent polymer is a fluorescent polymer).

This luminescent reagent includes the following aspects,

IV-1. The luminescent reagent according to IV, containing the biotin-labeled luminescent polymer according to any of the above-mentioned I and I-1 to I-12 in a state of being bound with avidin or streptavidin.

IV-2. The luminescent reagent according to IV or IV-1, which is used for labeling and detecting a target substance in bioassay.

IV-3. The luminescent reagent according to IV or IV-1, which is used for amplifying luminescent intensity in bioassay.

The present invention further relates to a reagent kit containing as a constituent component a luminescent reagent utilizing a biotin-labeled luminescent polymer, as given below.

V. A luminescent reagent kit, comprising at least the luminescent reagent according to any one of IV and IV-1 to IV-3 and a biotin-labeled substance capable of specifically binding to a target substance, or at least the luminescent reagent according to any one of IV and IV-1 to IV-3, a biotin-labeled substance capable of specifically binding to a target substance and avidin or streptavidin.

V-1. The luminescent reagent kit according to V, further comprising an insoluble carrier to which a substance capable of specifically binding the target substance is bound.

V-2. The luminescent reagent kit according to V or V-1, which is a reagent kit used for bioassay.

The present invention further relates to a bioassay method, carried out by using biotin-labeled luminescent polymer, as given below.

VI. A bioassay method for a target substance, comprising a step of:
    forming a complex of the biotin-labeled luminescent polymer according to any of I and I-1 to I-12 and the target substance, via avidin or streptavidin, and
    assaying the complex thus formed by detecting luminescence from the complex.
This bioassay method includes the following aspects.

VI-1. The bioassay method according to VI, wherein the chemiluminescent polymer or fluorescent polymer according to I-2 is used as the biotin-labeled luminescent polymer, and the luminescent detection means is a chemiluminescent detection means or fluorescent detection means.

VI-2. The bioassay method according to VI or VI-1, comprising the following steps (i), (ii), and (iii):
    (i) attaching a biotin to the target substance;
    (ii) complexing the biotin-labeled target substance obtained in step (i), avidin or streptavidin, and the biotin-labeled luminescent polymer according to any of I and I-1 to I-12; and
    (iii) assaying the complex obtained in step (ii) comprising the biotin-labeled target substance, the avidin or streptavidin, and the biotin-labeled luminescent polymer by detecting chemiluminescence or luminescence from the complex VI-3. The bioassay method according to VI-2, comprising a step prior to step (i) of fixing the target substance to an insoluble carrier.

VI-4. The bioassay method according to VI or VI-1, wherein the luminescent reagent according to IV-1 is used instead of the biotin-labeled luminescent polymer.

VI-5. The bioassay method according to VI-4, comprising the following steps (i), (ii), and (iii):
    (i) attaching a biotin to the target substance;
    (ii) complexing the biotin-labeled target substance obtained in step (i) and the luminescent reagent according to IV-1; and
    (iii) assaying the complex obtained in step (ii) comprising the biotin-labeled target substance, the avidin or streptavidin, and the biotin-labeled luminescent polymer by detecting chemiluminescence or fluorescence from the complex.

VI-6. The bioassay method according to VI-5, comprising a step prior to step (I) of fixing the target substance to an insoluble carrier.

VI-7. The bioassay method according to any of VI and VI-1 to VI-6, wherein the complex obtained in step (ii) in the above-mentioned VI-2 or VI-5 is a complex formed by binding two or more luminescent polymers according to any of I and I-1 to I-12 via avidin or streptavidin, and further binding the resulting complex to a biotin-labeled target substance via avidin or streptavidin.

VI-8. The bioassay method according to VI-7, which is used as a luminescent amplification method.

VII. A use of the biotin-labeled luminescent polymer of any of the above-mentioned I and I-1 to I-12 as a luminescent signal probe in bioassay.

VIII. A use of the biotin-labeled luminescent polymer of any of the above-mentioned I and I-1 to 1-12 to prepare a luminescent reagent in bioassay.

IX. A use of the luminescent reagent kit of any of V, V-1, and V-2 as a luminescent amplification reagent kit in bioassay.

Figure 1:
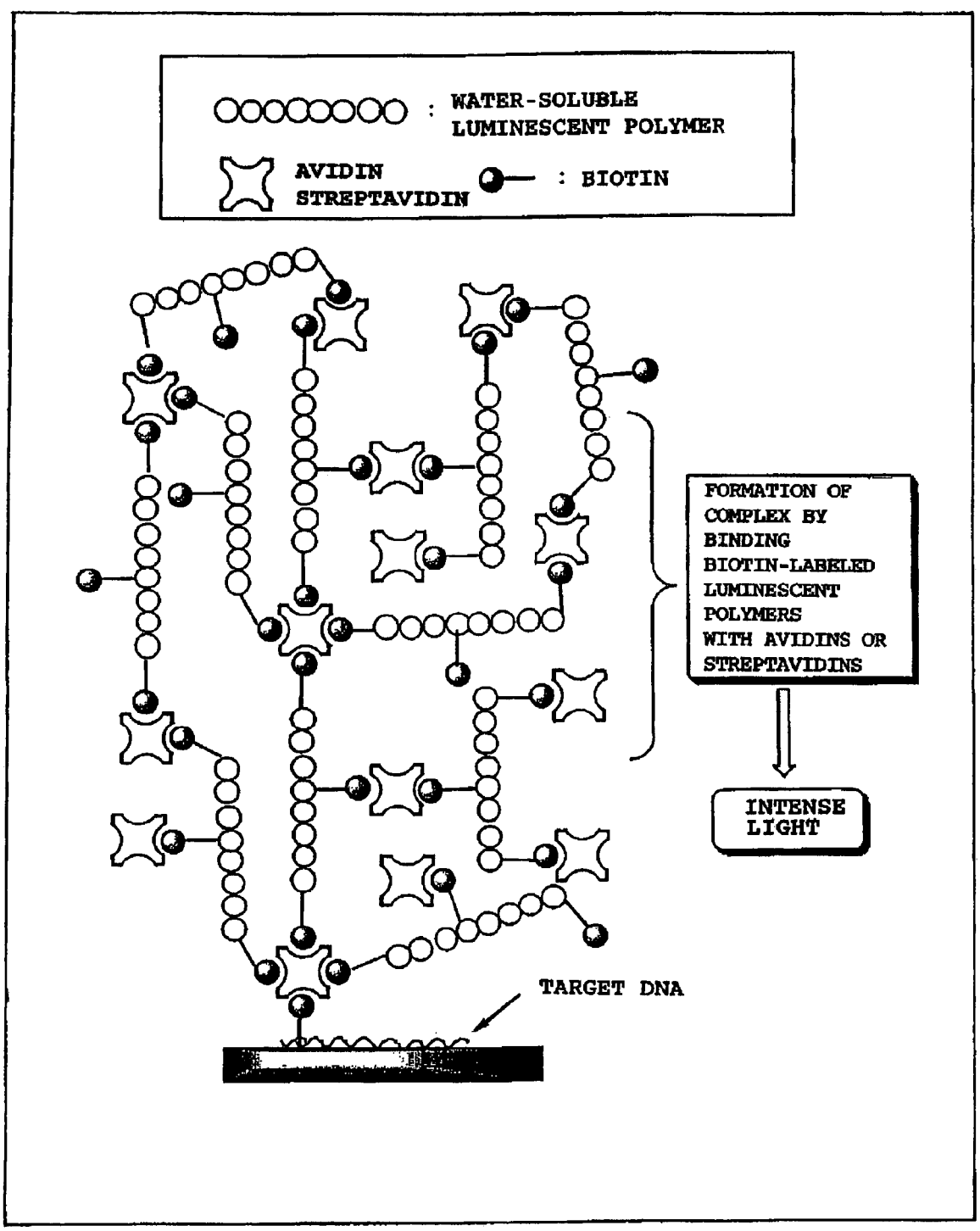
FIG. 1 is a schematic diagram, using DNA as an example of a target substance, of the principle for detecting a target substance using the biotin-labeled luminescent polymer of the present invention as a signal probe.

BEST MODE FOR CARRYING OUT THE INVENTION (1) Biotin-Labeled Luminescent Polymer

The biotin-labeled luminescent polymer of the present invention is a luminescent polymer comprising at least one biotin covalently attached to a polymer that includes as a constituent monomer a monosaccharide or an amino acid covalently attached to a luminescent substance.

(1-1) Luminescent Polymer

The polymer used in the preparation of the luminescent polymer includes one or more types of monosaccharide or amino acid as a constituent monomer, either the same or different. Specific examples include polysaccharides (polymers of monosaccharide) having one or more types of monosaccharide, and polyamino acids, peptides, polypeptides and proteins (a polymer of amino acids) having a repeated structure composed of one or more types of amino acid. It is preferable to use a biopolymer or a water-soluble polymer that is miscible on compatible with biocomponents.

There are no particular restrictions on the monosaccharide here as long as it is a constituent monomer of a polysaccharide and can form a cyclic structure, but common examples include pyranose having 5 carbons or furanose having 6 carbons. It does not really matter whether the monosaccharide is alpha or beta type. Specifically, examples include glucose, fructose, and oxides (such as galacturonic acid (galactopyranuronic acid)), but this list is not meant to be comprehensive.

Examples of favorable polysaccharides having these monosaccharide as a constituent monomer include dextran, pullulan, glycogen, inulin, and pectin. Dextran and pullulan are especially favorable.

There are no particular restrictions on the amino acid as long as it can serve as the constituent monomer of a polyamino acid, peptide, polypeptide, or protein, but examples include various kinds of amino acids that constitute protein and known amino acids other than the amino acids that constitute protein. It does not really matter whether the amino acid is a D- or L-amino acid, or an $\alpha$-, $\beta$-, or $\delta$-amino acid. Specific examples of amino acids other than protein constitutive amino acids include the amino acids discussed on pages 33 to 59 of "Seikagaku Detabukku I" [Biochemical Databook I] (ed. J. Biochem. Soc.) published by Tokyo Kagaku Dojin (Oct. 1, 1982).

Favorable polyamino acids having these amino acids as a constituent monomer include, but are not limited to, polymers of monoaminodicarboxylic acids such as aspartic acid, glutamic acid, and homoglutamic acid, and polymers of diaminomonocarboxylic acids such as lysine and $\delta$-hydroxylysine.

The polymer used in the present invention may be composed of just the above-mentioned monosaccharide or amino acid as monomer, or may include both a monosaccharide and an amino acid as monomer, or may include other constituent components besides a monosaccharide or amino acid.

There are no particular restrictions on the degree of polymerization of the monosaccharide or amino acid constituting the polymer, or on the molecular weight of the polymer. It is preferable that the luminescent polymer comprising a luminescent substance attached to a polymer, or the biotin-labeled luminescent polymer comprising at least one biotin further attached to the polymer is water-soluble, so that the degree of polymerization and a molecular weight of the polymer are unrestrained as long as the polymer remains water-soluble.

The term "water-soluble" as used here means that the solubility is at least 0.5 mg/mL when the subject material is dissolved in water or a neutral buffer. Defined from a practical standpoint, the above-mentioned luminescent polymer or biotin-labeled luminescent polymer being "water-soluble" refers to these polymers having enough solubility that they will not result in any precipitate or insoluble material when used as a fluorescent signal probe or the like in the present invention.

The luminescent substance used to label the monosaccharide or amino acid constituting this polymer is unrestricted as long as it either is self-luminous substance or is capable of emitting a light by some treatment, and the luminescence or the light can be detected by an optical detection means. Preferably, the luminescent substance is one that emits fluorescence itself (fluorescent substance), or is capable of emitting a light when is chemically oxidized (chemiluminescent substance). This luminescent substance also needs to be a compound that can be covalently attached directly or indirectly to a monosaccharide or an amino acid. Preferably, this is a compound that will not lose much of the water solubility required of the luminescent polymer of the present invention as a result of the labeling of the luminescent substance or as the number of labels on the luminescent substance increases. As long as the above requirement is satisfied, there are no particular restrictions on the molecular weight and so forth of the luminescent substance itself.

A wide range of luminescent substances that have been known in the past or are likely to be developed in the future can be used as the luminescent substance in the present invention, as long as the above requirement is satisfied. It is preferable to use the following cyanoisoindoles, luminols, and acridinium esters.

(I) Cyanoisoindoles

An example of cyanoisoindoles in the present invention is a compound having a cyanoisoindolyl (1-cyanoisoindol-2-yl) skeleton expressed by the following formula (1):

[Eighth Chemical Formula]

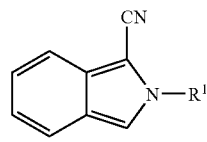

(1)

(where $R^1$ is any group).

This compound having a cyanoisoindolyl skeleton is a compound that emits fluorescence itself (fluorescent substance), and is also a chemiluminescent compound (chemiluminescent substance) capable of emitting light by treatment with hydrogen peroxide and acetonitrile in an alkaline sodium borate buffer at room temperature.

In Formula (1) above, there are no particular restrictions on the substituent $R^1$ as long as the cyanoisoindoles have the properties discussed above. However, when the cyanoisoindoles are used for attaching to a polymer discussed below, examples of the substituent $R^1$ include a functional group that can attach to a monosaccharide or an amino acid that is a constituent monomer of the polymer, and particularly a functional group that can attach to a ring-opened aldehyde group of the monosaccharide or with a carboxyl group or amino group of the amino acid, such as a functional group including an amino group ($-NH_2$), a halogen group, an isothiocyanate group ($-NCS$), a hydrazinocarbonyl group ($-CO-NHNH_2$), a hydrazino group ($-NHNH_2$), or a succinimidyloxycarbonyl group expressed by the following formula:

[Ninth Chemical Formula]

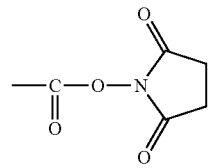

(II) Luminols

The luminols in the present invention refer to compounds having a phthalhydrazide (1,4-dihydroxyphthalazine) skeleton expressed by the following formula (2):

[Tenth Chemical Formula]

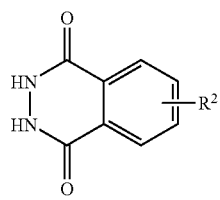

(2)

(where $R^2$ is any group).

Specific examples include phthalhydrazide (also known as phthalazinedione and 1,4-dihydroxyphthalazine) compounds in which at least one hydrogen atom at the 5, 6, 7, or 8 position, and preferably at least one hydrogen atom at the 5 or 6 position, has been substituted with another functional group.

This compound having a phthalhydrazide skeleton may be a compound that emits fluorescent itself (fluorescent substance), and is also a chemiluminescent compound (chemiluminescent substance) capable of emitting light by treating with hydrogen peroxide and a suitable oxidation catalyst (such as peroxydase, a heavy metal, or a cyanide) in a neutral or alkaline buffer at room temperature. There are no particular restrictions on the substituent $R^2$ in the above Formula (2) as long as the luminols have the properties discussed above, but when the luminols are used for attaching to a polymer discussed below, examples of the substituent $R^2$ include a functional group that can attach to a monosaccharide or an amino acid that is a constituent monomer of the polymer, and particularly a functional group that can attach to a ring-opened aldehyde group of the monosaccharide or with a carboxyl group or amino group of the amino acid, such as a functional group including an amino group, a halogen group, an isothiocyanate group, a hydrazinocarbonyl group, a hydrazino group, or a succinimidyloxycarbonyl group.

Commercially available luminols (2) include luminol ($R^2=NH_2$; 5-amino-2,3-dihydro-1,4-phthalazinedione), isoluminol ($R^2=NH$, 6-amino-2,3-dihydro-1,4-phthalazinedione), and the N-(4-aminobutyl)-N-ethylisoluminol expressed by the following formula.

[Eleventh Chemical Formula]

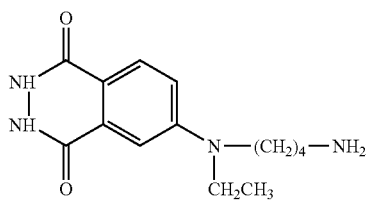

(III) Acridinium Esters

The acridinium esters in the present invention include a compound (10-methyl-9-alkyloxycarbonylacridine) having a structure expressed by the following formula (3):

[Twelfth Chemical Formula]

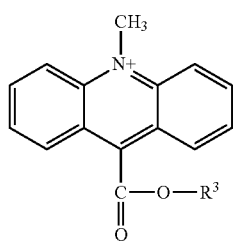

(3)

(where $R^3$ is any group).

This acridinium esters (3) may include a compound that emits fluorescent itself (fluorescent substance), and include also a chemiluminescent compound (chemiluminescent substance) capable of emitting light in an alkaline aqueous solution and hydrogen peroxide by hydrolysis of the ester attached to the acridine. In the above Formula (3), there are no particular restrictions on the substituent $R^3$ as long as the acridinium esters have the properties discussed above, but when the acridinium esters are used for attaching to a polymer discussed below, examples of the substituent $R^3$ include a functional group that can attached to a monosaccharide or an amino acid that is a constituent monomer of the polymer, and particularly a functional group that can attach to a ring-opened aldehyde group of the monosaccharide or with a carboxyl group or amino group of the amino acid, such as a functional group including, an amino group a halogen group, an isothiocyanate group, a hydrazinocarbonyl group, a hydrazino group, or a succinimidyloxycarbonyl group. Acridinium esters with a variety of functional groups at the $R^3$ position have already been reported (R. Renotte et al., Luminescence, 15, 311-320 (2000)) and known in public.

The luminescent polymer that is the object of the present invention is a luminescent polymer including as a constituent monomer the above-mentioned luminescent substance covalently attached to the above-mentioned monosaccharide or amino acid. Preferably, it is a polymer of a monosaccharide (polysaccharide) or a polymer of an amino acid (polyamino acid, peptide, polypeptide, or protein) having a monosaccharide or amino acid to which the above-mentioned luminescent substance is covalently attached.

All of the monomers constituting this luminescent polymer may be monosaccharides or amino acids labeled with the above-mentioned luminescent substance, but this not necessarily the case, and labeled monomers (labeled monosaccharides or amino acids) and unlabeled monomers (unlabeled monosaccharides or amino acids) may be mixed together in the polymer. There are no particular restrictions on the proportion of monomers labeled with a luminescent substance contained in the luminescent polymer, as long as the water solubility of the polymer being used as a backbone is not markedly reduced and the resulting luminescent polymer remains water-soluble. Although it will vary with the type of polymer used, for instance, the proportion of monomers labeled with the luminescent substance is usually no more than half of the total number of monomers constituting the polymer, and preferably from 30 to 50%.

There are no particular restrictions on the method for manufacturing the luminescent polymer used in the present invention, but examples include a method in which the monomers (monosaccharides or amino acids) constituting the polymer are first labeled with the above-mentioned luminescent substance and then polymerized, and a method in which a polymer containing a monosaccharide or amino acid as a constituent monomer (and preferably a polymer of a monosaccharide or a polymer of an amino acid) is reacted with a luminescent substance so as to introduce a luminescent substance into two or more monosaccharides or amino acids in the polymer. The latter method is preferred. The following are examples of manufacturing methods.

① When a polysaccharide is used as the polymer, and any of cyanoisoindoles (1), luminols (2), and acridinium esters (3) is used as the luminescent substance, for instance, the luminescent polymer can be manufactured according to scheme A expressed by the following formulas.

[Thirteenth Chemical Formula]

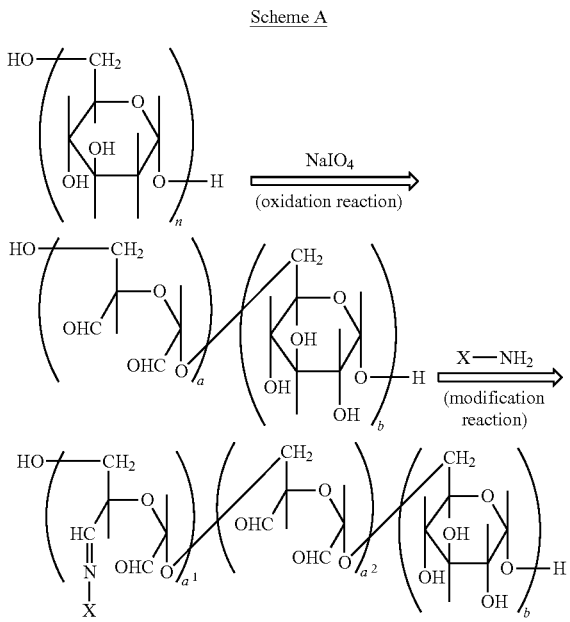

In the formulas, n is any natural number greater than or equal to 5. a and b are numbers that satisfy the relationships $n=a+b$ ($a \geq 1$, $b \geq 0$) and $a=a^1+a^2$ ($a^1 \geq 1$, $a^2 \geq 0$). Also, X—$NH_2$ in the formulas is a luminescent substance, and more specifically a luminescent substance having a functional group (—$NH_2$) for binding to a monosaccharide. More specifically, X—$NH_2$ is any of cyanoisoindoles expressed by the following formula (7);

[Fourteenth Chemical Formula]

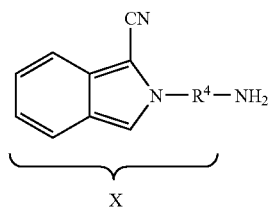

(where $R^4$ is a spacer),
luminols expressed by the following formula (8):
[Fifteenth Chemical Formula]

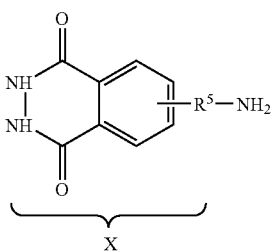

(where $R^5$ is a single bond or a spacer),
or acridinium esters expressed by the following formula (9):
[Sixteenth Chemical Formula]

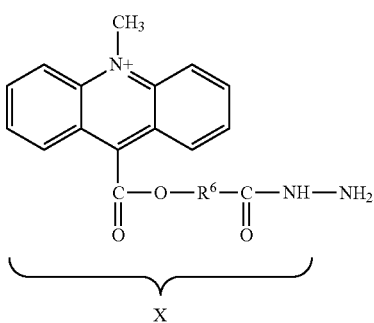

(where $R^6$ is a single bond or a spacer).

The $R^4$—$NH_2$ in the cyanoisoindoles expressed by Formula (7) above corresponds to a case when the $R^1$ of the cyanoisoindoles expressed by Formula (1) is a functional group is an amino group, the $R^5$—$NH_2$ in the luminols expressed by Formula (8) above corresponds to a case when the $R^2$ of the luminols expressed by Formula (2) is a functional group is an amino group, and the $R^6$—CO—NH—$NH_2$ in the acridinium esters expressed by Formula (9) above corresponds to a case when the $R^3$ of the acridinium esters expressed by Formula (3) is a functional group is an amino group, a hydrazino group, or a hydrazinocarbonyl group.

Here, n is the degree of polymerization of the monosaccharide in the polysaccharide used as the polymer. The greater is the degree of polymerization of the monosaccharide, the greater is the number of the luminescent substance attached to the monosaccharides, so it is preferable for n to be greater. There are no particular restrictions on this number, but it is preferable that a degree of polymerization that the resulting polymer maintains water solubility. A natural number of at least 5 is usually good, but favorable examples include natural numbers from 10 to 10,000.

There are no particular restrictions on the spacers indicated by $R^4$, $R^5$, and $R^6$ in Formulas (7), (8), and (9), respectively, but these can be selected from one such that the compounds respected in Formulas (7), (8), and (9) have luminescence without being markedly lost the inherent luminescence from the cyanoisoindoles (1), the luminols (2), and the acridinium esters (3). The preferable spacer is one such that a luminescent polymer prepared by binding any of these compounds (7), (8), and (9) with a polymer has the desired water solubility without being markedly lost water solubility from the polymer. Examples of these spacers include a hydrocarbon chain in which a hetero atom may be interposed. All or part of the hydrocarbon chain may be cyclic. Preferable examples include linear hydrocarbon chains such as an alkylene group, an alkenylene group, an alkadienylene group, and an alkynylene group, and cyclic hydrocarbon chains such as a cycloalkylene group, a cycloalkenylene group, a cycloalkadienylene group, and a phenylene group. Particularly favorable linear hydrocarbon chain is an alkylene group, and particularly favorable cyclic hydrocarbon chain is a phenylene group. These may have side chains if desired. The spacers may be composed of just linear hydrocarbon chains or cyclic hydrocarbon chains, or may include a combination of both.

Favorable examples of the spacer indicated by $R^4$ in the cyanoisoindoles (7) include an alkylene group and a phenylene group. An example of the cyanoisoindoles (7) when $R^4$ is an alkylene group is the N-(aminoalkyl)-1-cyanoindole expressed by the following formula:
[Seventeenth Chemical Formula]

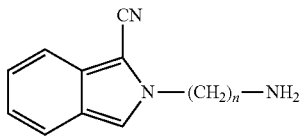

and an example of the cyanoisoindoles (7) when $R^4$ is a phenylene group is the N-(aminophenyl)-1-cyanoindole expressed by the following formula:
[Eighteenth Chemical Formula]

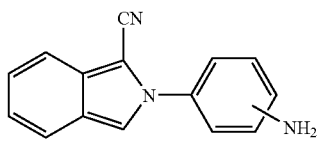

Examples of the alkylene groups mentioned here include linear and branched alkylene groups having $C_1$ to $C_6$ linear hydrocarbon chains. It is preferable to use a $C_1$ to $C_6$ lower alkylene group. Specific examples include a methylene group, ethylene group, butylene group, isobutylene group, propylene group, isopropylene group, pentamethylene group, hexamethylene group, and cyclohexanediyl group.

In the luminols (8), $R^5$ stands for a single bond or a spacer. Specifically, this spacer refers to an —NH—$(CH_2)$n- group, —NH—$(CH_2)$n-Ph- group (where -Ph- indicates a phenylene group; the same applies hereinafter in this Specification), —NH—$(CH_2)$n-NH— group, —NH—$(CH_2)$n-Ph-$(CH_2)$n-

NH— group, or N-(4-alkylene)-N-alkyl group (such as an N-(4-butylene)-N-ethyl group). Examples of the alkylene group expressed by —(CH$_2$)n- here include linear and branched alkylene groups having C$_1$ to C$_6$ (n=1 to 6) linear hydrocarbon chains, just as above, with a lower alkylene group being preferable. Examples of the luminols (8) when R$^5$ is a single bond include a luminol and an isoluminol, while examples of the luminols (8) when R$^5$ is a spacer include the N-(4-aminobutyl)-N-ethylisoluminol expressed by the following formula.

[Nineteenth Chemical Formula]

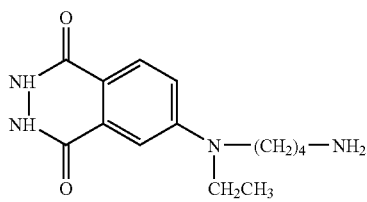

the N-(p-hydrazinomethylene)benzylisoluminol expressed by the following formula:

[Twentieth Chemical Formula]

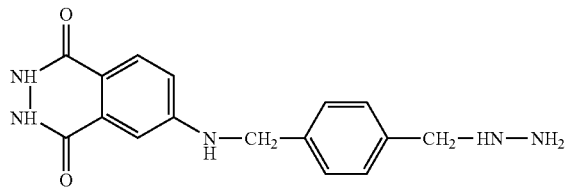

and the N-(5'-hydrazinopentamethylene)isoluminol expressed by the following formula:

[Twenty-First Chemical Formula]

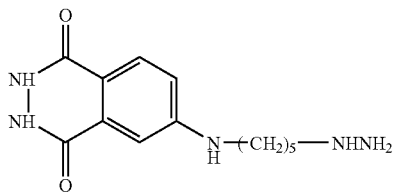

These luminols are all commercially available or can be manufactured.

If R$^5$ is a spacer in the —R$^5$—NH$_2$ group here, this group may be located in the 5 or 6 position of the phthalhydrazide skeleton. R$^5$ is not limited to the specific examples given above, and it is also possible to use luminols in which the —R$^5$—NH$_2$ group is a functional group having an amino group that can attach to a monomer constituting the polymer, such as a monosaccharide or amino acid.

R$^6$ is a single bond or a spacer in the acridinium esters (9). A specific example of a spacer is a -Ph-(CH$_2$)n- group. Examples of acridinium esters (9) corresponding to this include the hydrazide derivatives expressed by the following formula:

[Twenty-Second Chemical Formula]

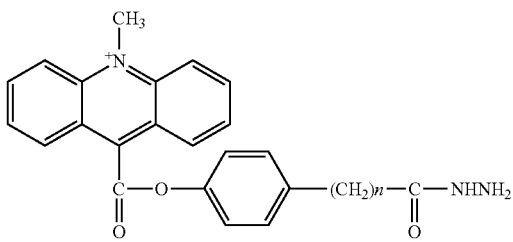

Examples of the alkylene group "—(CH$_2$)n-" in the -Ph-(CH$_2$)n- group here include linear and branched alkylene groups having C$_1$ to C$_6$ (n=1 to 6) linear hydrocarbon chains. A C$_1$ to C$_6$ lower alkylene group is preferable. Specific examples include a methylene group, ethylene group, butylene group, isobutylene group, propylene group, isopropylene group, pentamethylene group, and hexamethylene group.

As shown by the following formula:
[Twenty-Third Chemical Formula]

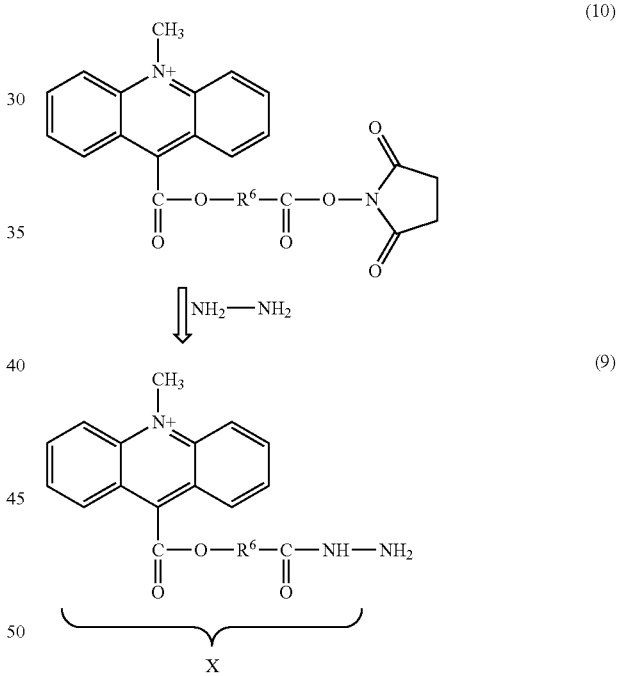

(where R$^6$ is a spacer; -Ph-(CH$_2$)n- is given as an example here), the acridinium esters (9) (the above-mentioned hydrazide derivative) can be prepared, for example, by reacting commercially available 10-methyl-9-4-[2-(succinimidyloxycarbonyl)alkyl]phenyloxycarbonyl acridinium (10) with hydrazine (NH$_2$—NH$_2$) for about 10 minutes to 2 hours at 4° C., for instance, in an aprotic solvent such as acetonitrile, tetrahydrofuran, dimethylformamide, or dimethyl sulfoxide.

The method for manufacturing the luminescent polymer (6) shown in Scheme A above is specifically carried out as follows. First, a polysaccharide (4) is oxidized to open all or some of the rings of cyclic monosaccharides constituting the polysaccharide and form a polysaccharide having aldehyde groups (5) (the aldehyde group is referred to as "ring-opened aldehyde group" in this specification). Secondly, an amino group of the luminescent substance indicated by X—$NH_2$ (such as cyanoisoindoles (7), luminols (8), or acridinium esters (9)) attaches through a dehydrative condensation to the ring-opened aldehyde group.

The above-mentioned oxidation reaction for opening the monosaccharide should involve the oxidative decomposition of the carbon-carbon bonds of the sugar. Specifically, this can be accomplished by reacting the polysaccharide (4) with an oxidant such as sodium periodate in water or a suitable aqueous solvent. There are no restrictions on this reaction, but it can be conducted at a temperature of 4 to 37° C., and preferably about 25° C., and the reaction is usually completed in 0.5 to 5 hours. The labeling of the polysaccharide with the luminescent substance can be accomplished by reacting the ring-opened polysaccharide (5) obtained at the first step in the above reaction with the luminescent substance in the presence of an acid such as acetic acid in ethylene glycol, dimethyl sulfoxide, or a suitable aqueous solvent. There are no restrictions on this reaction, but it can be conducted at a temperature of 25 to 80° C., and preferably about 60° C., and the reaction is usually completed in 6 to 48 hours.

The luminescent polymer (6) encompasses both random and block polymers comprising of the monomer (monosaccharide or amino acid) to which the luminescent substance is covalently attached and the monomer (monosaccharide or amino acid) to which the luminescent substance is not covalently attached.

② When a polyamic acid (such as polymers of aspartic acid, glutamic acid, and homoglutamic acid) produced by the polymerization of a monoaminocarboxylic acid is used as the polymer, and any of cyanoisoindoles (1), luminols (2), and acridinium esters (3) are used as the luminescent substance, the luminescent polymer can be manufactured according to scheme B represented by the following formulas.

[Twenty-Fourth Chemical Formula]

Scheme B

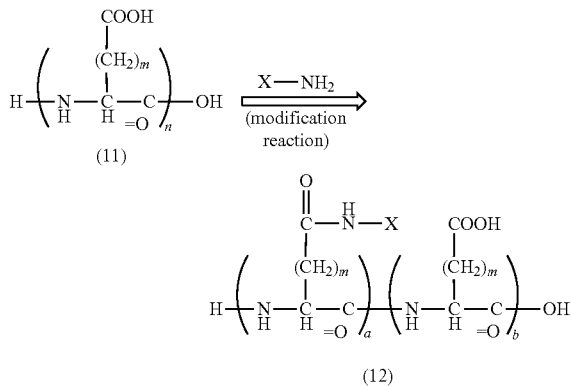

(11)

(12)

In the formulas, m is a natural number from 1 to 3, and n is any natural number greater than or equal to 5. a and b are numbers that satisfy the relationship n=a+b (a≧1, b≧0). X—$NH_2$ is defined the same as above.

Here, n is the polymerization degree of amino acid in the polyamino acid used as the polymer. As described above for when the polymer was a polysaccharide, the greater is the polymerization degree of the amino acid, the greater is the number of the luminescent substance bound to the amino acids, so it is preferable for n to be greater. It is preferable that a degree of polymerization that the resulting polymer maintains water solubility. A natural number of at least 5 is usually good, but favorable examples include natural numbers from 10 to 10,000.

In Scheme B above, the labeling of the polyamino acid (11) with the luminescent substance (X—$NH_2$) having an amino group can be accomplished by attaching the amino group of the luminescent substance, such as the above-mentioned cyanoisoindoles (7), luminols (8), or acridinium esters (9), to a carboxyl group of the polyamino acid (11) to form an acid amide linkage (—CONH— linkage).

The acid amide linkage here can be formed by reacting the polyamino acid (11) with the luminescent substance (X—$NH_2$) in the presence of a condensing agent such as N,N'-dicyclohexylcarbodiimide (DCC) in dimethylformamide or another suitable solvent. There are no restrictions on this reaction, but it can be conducted at a temperature of 4 to 60° C., and preferably about 37° C., and the reaction is usually completed in 1 to 24 hours.

③ When a polyamic acid (polymers such as polylysine and poly-δ-hydroxylysine) produced by the polymerization of a diaminomonocarboxylic acid is used as the polymer, and any of cyanoisoindoles (1) or luminols (2) are used as the luminescent substance, the luminescent polymer can be manufactured according to scheme C represented by the following formulas. The following formula is an example of using a polymer of lysine (polylysine) as the polyamino acid, but polymers of other diaminomonocarboxylic acids can be similarly used.

[Twenty-Fifth Chemical Formula]

Scheme C

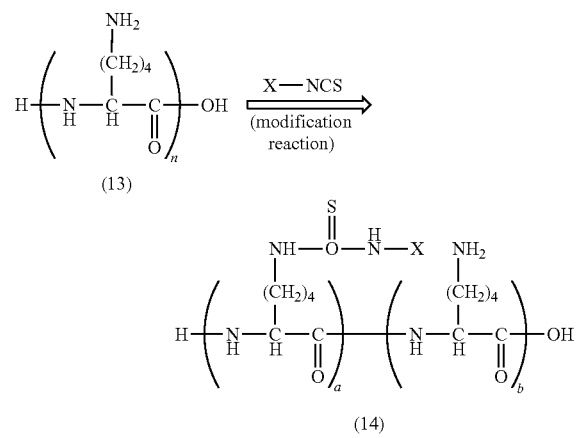

(13)

(14)

In the formulas, n is any natural number greater than or equal to 5. a and b are numbers that satisfy the relationship n=a+b (a≧1, b≧0). X—NCS is a luminescent substance having an isocyanate group, which is a group attaching to an amino acid, and more specifically X—NCS is an isothiocyanic acid derivative (15) of cyanoisoindoles expressed by the following formula:

[Twenty-Sixth Chemical Formula]

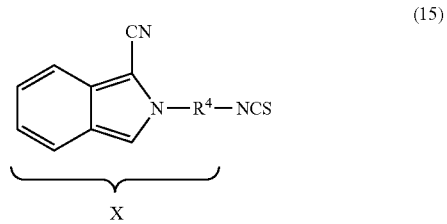

(15)

(where $R^4$ is defined the same as above), or an isothiocyanic acid derivative (16) of luminols expressed by the following formula:

[Twenty-Seventh Chemical Formula]

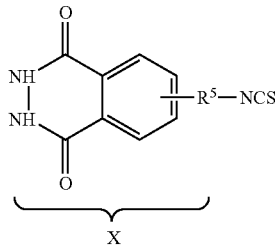

(16)

(where $R^5$ is defined the same as above).

The above-mentioned isothiocyanic acid derivative (15) of cyanoisoindoles corresponds to a case when the $R^1$ of the cyanoisoindoles expressed by Formula (1) is a functional group having an isocyanate group, and the isothiocyanic acid derivative (16) of luminols corresponds to a case when the $R^2$ of the luminols expressed by Formula (2) is a functional group having an isothiocyanate group.

The isothiocyanic acid derivative (15) or (16) can be prepared by reacting the amino groups of the cyanoisoindoles expressed by Formula (7) or of the luminols expressed by Formula (8), respectively, with thiophosgene in an aprotic solvent such as tetrahydrofuran or benzene. There are no restrictions on this reaction, but it can be conducted at a temperature of 25 to 60° C., and preferably about 60° C., and the reaction is usually completed in 0.1 to 10 hours.

In Scheme C above, the labeling of the polyamino acid (13) with the luminescent substance (X—NCS) can specifically be accomplished by attaching the isothiocyanate groups of the isothiocyanic acid derivative (15) or (16) prepared by the above method to the amino groups of the polyamino acid (13). There are no restrictions on this reaction, but it can be conducted at a temperature of 25 to 60° C., and preferably about 60° C., under the presence of organic salts such as pyridines and the reaction is usually completed in 0.1 to 10 hours.

④ When any of acridinium esters (3) is used instead of the above-mentioned cyanoisoindoles (7) or luminols (8) as the luminescent substance, the luminescent polymer can be manufactured according to scheme D depicted by the following formulas. These formulas are examples of when a polymer of lysine (polylysine) is used as the polyamino acid, but the same scheme applies to polymers of other diaminomonocarboxylic acids.

[Twenty-Eighth Chemical Formula]

Scheme D

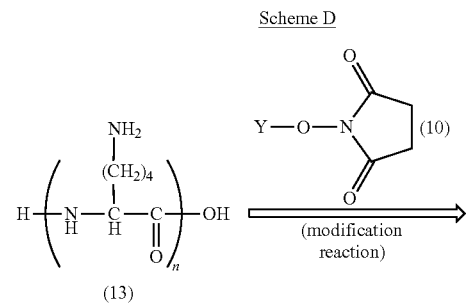

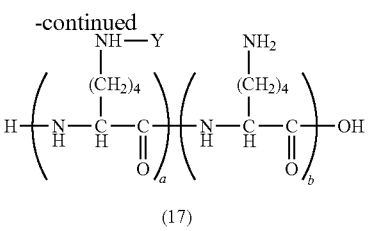

(17)

In the formulas, n is any natural number greater than or equal to 5. a and b are numbers that satisfy the relationship n=a+b (a≧1, b≧0). The compound expressed by Formula (10) in the Scheme D is acridinium ester (10-methyl-9-4-[2-(succinimidyloxycarbonyl)alkyl]phenyloxycarbonyl acridinium) expressed by the following formula:

[Twenty-Ninth Chemical Formula]

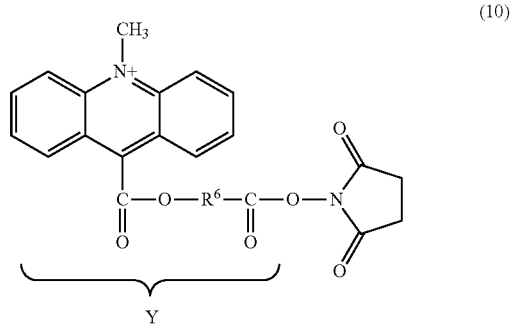

(10)

(where $R^6$ is a spacer, and here -Ph-(CH$_2$)n- is given as an example).

In Scheme D above, the labeling of the polyamino acid (13) with the luminescent substance can specifically be accomplished by attaching an active ester group (the group expressed by Y in Formula (10)) of the luminescent substance (the 10-methyl-9-4-[2-(succinimidyloxycarbonyl)-alkyl] phenyloxycarbonyl acridinium (10) is used here), which has another group attaching to an amino acid other than Y, to an amino group of the polyamino acid (13). This reaction can be conducted by reacting the acridinium esters (10) with the polyamino acid (13) in an aprotic solvent or a weakly alkaline aqueous solution. Dimethylformamide, tetrahydrofuran, acetonitrile, or the like can be used as the aprotic solvent here.

There are no restrictions on this reaction, but it can be conducted at a temperature of 4 to 60° C., and preferably about 25° C. and the reaction is usually completed in 0.1 to 10 hours.

With the various manufacturing methods given above in Schemes A to D, as mentioned above, the luminescent substance may be attached to all of the various monomers (monosaccharide or amino acid) constituting the polymer (in the case of Scheme A, b=0, $a^2$=0, n=$a^1$; in the case of Schemes B to D, b=0, n=a), or the luminescent substance may be attached to just some of the monomers (in the case of Scheme A, b≧1 or $a^2$≧1, n=$a^1$+$a^2$+b; in the case of Schemes B to D, b≧1, n=a+b). The number of bonds of luminescent substance to the polymer is preferably within a range such that the water solubility of the polymer will not be lost as a result of the attachment of the luminescent substance, and can be suitably adjusted within this range. Preferably, the number of monomers labeled with luminescent substance ($a^1$ in the case of Scheme A, a in the case of Schemes B to D) is no more than half the total number of monomers (n), and even more preferably from 30 to 50%. The number of luminescent substance attached to the polymer can be controlled as desired by suitably adjusting the binding reaction conditions between the luminescent substance and the polymer.

The luminescent polymer obtained by the above methods can be separated from the reaction system and further purified by standard means known in the past, as needed. Examples of such purifying methods include column chromatography, solvent elution, and reprecipitation.

(1-2) Biotin-Labeled Luminescent Polymer

The above-mentioned luminescent polymer can be effectively utilized as a luminescent signal probe in bioassay and other such measurement systems, for example. To utilize the above-mentioned luminescent polymer as a luminescent signal probe, it is preferable for means to be provided such that the luminescent polymer and the target substance can form specific bonds, either directly or indirectly, so that the target substance in question can be specifically detected. Examples of methods for forming specific bonds include a use of a so-called binder for specifically binding the target substance to the above-mentioned luminescent polymer. The binder that is attached to the luminescent polymer should be one having the property of forming specific bonds, either directly or indirectly, with the target substance to be detected, and can be any kind that utilizes the specific bindability among components, such as in the relationships between antigens and antibodies, biotin and avidin or streptavidin, first antibodies and second antibodies, hapten and anti-hapten antibodies, sense chains and antisense chains in oligo(poly)nucleotides, receptors and ligands, saccharide chains and lectin, enzymes and bases, and so forth, and has been used in conventional bioassay. When the target substance is a nucleic acid, specific examples of this binder include oligo(poly)nucleotides having a complementary base sequence of the base sequence of the nucleic acid of the target substance; when the target substance is an antigen (or antibody), examples include antibodies (or antigens) that specifically recognize that antigen (or antibody); when the target substance is labeled with avidin or streptavidin, examples include biotin; and when the labeling is labeled with a first antibody, an example is a second antibody.

The present invention in particular provides a biotin-labeled luminescent polymer comprising biotin covalently attached to a luminescent polymer using biotin as the binder discussed above.

There are no particular restrictions on the number of biotins attached to a single molecule of the luminescent polymer here, but two or more is preferable to just one, and more specifically, 2 to 50, 2 to 30, or 2 to 10, for example. Attaching two or more biotins to the luminescent polymer allows many luminescent polymers to be bound together via avidin or streptavidin, which makes it possible to amplify the luminescent intensity. The number of biotins attached to one molecule of the luminescent polymer is not limited to the specific numbers given above, and can be experimentally selected and adjusted in view of relationship between the luminescent substance, the polymer, the avidin or streptavidin, and other components constituting the measurement system.

There are no particular restrictions on how the biotin is attached to the luminescent polymer, and any standard method for the attachment of biotin can be employed.

For example, if the luminescent polymer is a polysaccharide (6), the biotin can be attached to the luminescent polymer (6) according to Scheme E expressed by the following formulas:

[Thirtieth Chemical Formula]

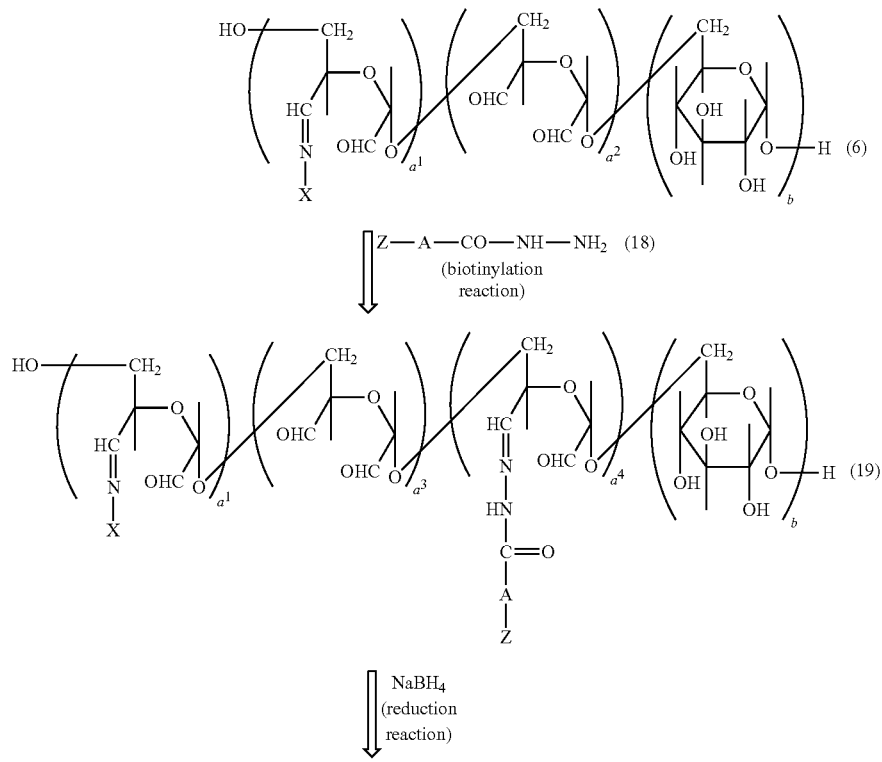

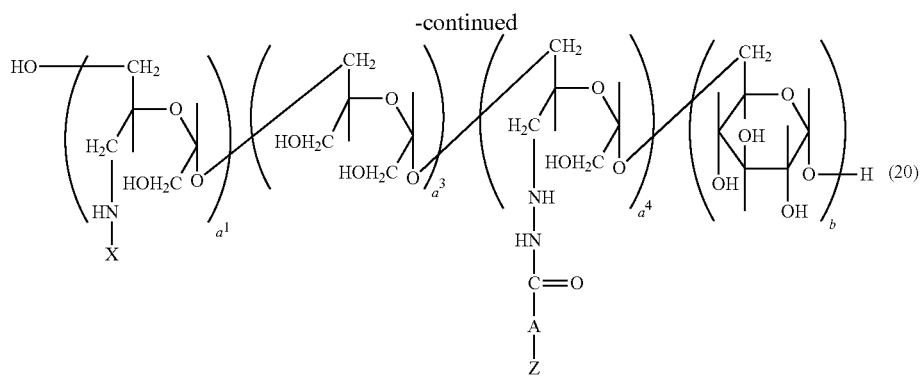

(where X, $a^1$, $a^2$ and b are defined the same as above; $a^3$ and $a^4$ are integers that satisfy the relationship $a^2=a^3+a^4$; $a^1 \geq 1$, $a^2 \geq 0$, $b \geq 0$, $a^3 \geq 0$ and $50 \geq a^4 \geq 2$; and Z in the hydrazide derivative of biotin expressed by Formula (18) is a biotin residue expressed by the following formula;

[Thirty-First Chemical Formula]

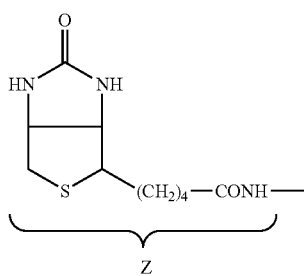

and A is a spacer).

In more specific terms, the biotin-labeled luminescent polymer (19) can be manufactured by first reacting the luminescent polysaccharide (6) obtained in manufacturing method ① shown in Scheme A above with a hydrazide derivative (18) of biotin comprising a hydrazinocarbonyl group attached via the spacer A to the biotin residue Z in a suitable solvent such as ethylene glycol or dimethylformamide, and secondly attaching the hydrazino groups (—NH—$NH_2$) of the hydrazide derivative (18) of biotin to the ring-opened aldehyde groups of the monosaccharide produced by the oxidation of the polysaccharide (6). The biotin-labeled luminescent polymer (19) produced by the above reaction can also be stabilized to form a compound (20), by dissolving the polymer (19) in an alcohol solvent (such as ethylene glycol) and reducing it with a reducing agent such as sodium borohydride.

The hydrazide derivative (18) of biotin used here can be any commercially available compound. For instance, it can be biotinamido hexanoic acid hydrazide (Sigma) having —$(CH_2)_5$— as the spacer indicated by A in Formula (18), or biotinhydrazide hexanoic acid hydrazide having —NH$(CH_2)_5$— as the spacer.

When the luminescent polymer is a polyamino acid (12) comprising a polymerized monoaminodicarboxylic acid, biotin can be attached to the luminescent polymer (12) according to Scheme F expressed by the following formulas:

[Thirty-Second Chemical Formula]

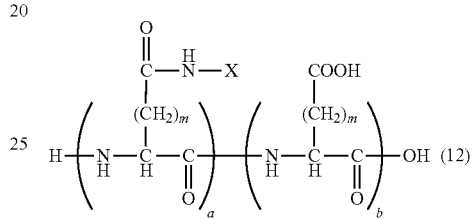

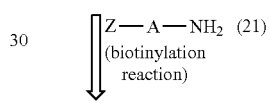

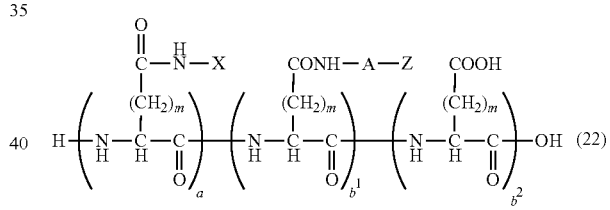

(where X, m, a, b, Z, and A are defined the same as above; $b^1$ and $b^2$ are integers that satisfy the relationships $b=b^1+b^2$, $50 \geq b^1 \geq 2$, and $b^2 \geq 0$).

In specific terms, the biotin-labeled luminescent polymer (22) can be manufactured by first reacting the polyamino acid (12) obtained in manufacturing method ② expressed in Scheme B above with the amine derivative (21) of biotin comprising an amino group attached via the spacer A to the biotin residue Z in a suitable solvent such as dimethylformamide, and secondly attaching the amino group of the amine derivative (21) of biotin to the free carboxyl group of the monoaminodicarboxylic acid constituting the polyamino acid (12).

The amine derivative (21) of biotin used here can be any commercially available compound. For instance, it can be biotinamidopentylamine having —$(CH_2)_5$— as the spacer A, or biotinhydrazide pentylamine having —NH$(CH_2)_5$— as the spacer A.

Furthermore, when the luminescent polymer is a polyamino acid (14) comprising a polymerized diaminomonocarboxylic acid, biotin can be attached to the luminescent polymer (14) according to Scheme G expressed by the following formulas:

[Thirty-Third Chemical Formula]

Scheme G

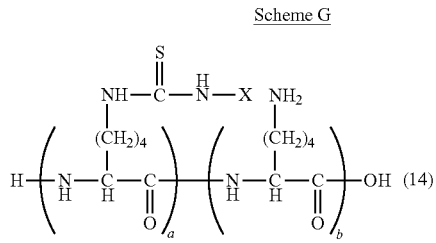

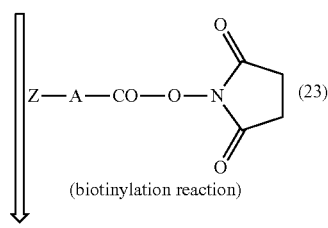

(biotinylation reaction)

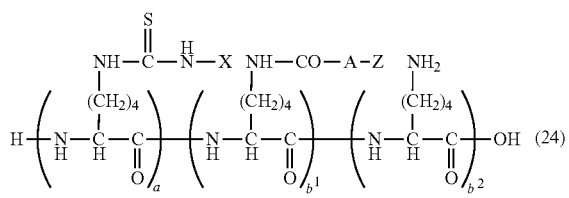

(where X, a, b, b$^1$, b$^2$, Z, and A are defined the same as above).

In specific terms, the biotin-labeled luminescent polymer (24) can be manufactured by first reacting the polyamino acid (14) obtained in manufacturing method ③ expressed in Scheme C above with the succinimide derivative (23) of biotin comprising a succinimidyloxycarbonyl group bound via the spacer A to the biotin residue Z in a suitable solvent such as tetrahydrofuran or dimethylformamide, and secondly attaching the carbonyl groups of the succinimide derivative (23) of biotin to the free amino groups of the water-soluble polyamino acid (14).

The succinimide derivative (23) of biotin used here can be any commercially available compound. For instance, it can be a biotinamido hexanoic acid N-hydroxy succinimide ester (Sigma) having —(CH$_2$)$_5$— as the spacer A, or a biotinhydrazide hexanoic acid N-hydroxy succinimide ester having —NH(CH$_2$)n- as the spacer A.

When the luminescent polymer is a polyamino acid (17) produced by polymerizing diaminomonocarboxylic acids, biotin can be attached to the luminescent polymer (17) according to Scheme H expressed by the following formulas:

[Thirty-Fourth Chemical Formula]

Scheme H

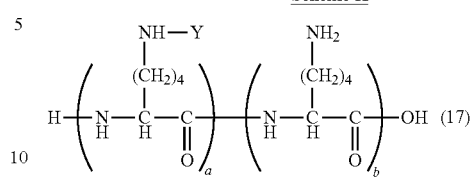

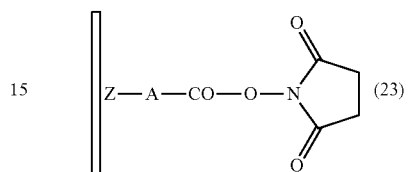

(biotinylation reaction)

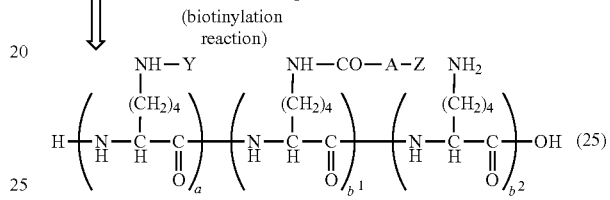

(where Y, a, b, b$^1$, b$^2$, Z, and A are defined the same as above).

In this case, other than using the compound (17) obtained in manufacturing method ④ expressed in Scheme D above as the luminescent polymer, everything can be carried out in the same manner as in the method of Scheme G above.

The biotin-labeled luminescent polymer obtained by the above methods can be separated from the reaction mixture and further purified by standard means known in the past, as needed. Examples of such purifying methods include the various methods listed above for the luminescent polymer. Avidin or streptavidin that specifically binds to biotin can also be utilized here.

Preferably, the biotin-labeled luminescent polymer is a compound (19) or reduced product (20) thereof, in which the polymer includes monosaccharide as a constituent monomer; at least one luminescent substance selected from the group consisting of cyanoisoindoles (7) having an amino group, luminols (8) having an amino group, and acridinium esters (9) having an amino group is attached through a dehydrative condensation to a ring-opened aldehyde group produced by the oxidation of the monosaccharide; and a hydrazino group of a hydrazide derivative (18) of biotin is attached to a ring-opened aldehyde group produced by the oxidation of another monosaccharide. This biotin-labeled luminescent polymer (19 or 20) comprising of a polysaccharide as a backbone polymer can be manufactured by a manufacturing method comprising the following steps (c) and (d).

(c) A step of attaching by a dehydrative condensation at least one luminescent substance selected from the group consisting of cyanoisoindoles (7) having a primary amino group, luminols (8) having a primary amino group, and acridinium esters (9) having a primary amino group to a ring-opened aldehyde group of monosaccharide produced by the oxidation of the polysaccharide: and (d) A step of attaching a hydrazino group of a hydrazide derivative (18) of biotin to another ring-opened aldehyde group produced by the oxidation of another monosaccharide of the polysaccharide.

The above step (c) corresponds to Scheme A above, while step (d) corresponds to Scheme E above. There are no particular restrictions on the order in which steps (c) and (d) are carried out, and step (d) may be performed after step (c), or vice versa.

(2) Use of the Biotin-Labeled Luminescent Polymer in Bioassay (2-1) Luminescent Signal Probe The biotin-labeled luminescent polymer of the present invention obtained as above can be bound directly or indirectly to the target substance to be measured, via a reaction with avidin or streptavidin. "Direct binding" here refers, for example, to a case in which an antibody that specifically recognizes an antigen, which is the target substance, is itself labeled by avidin or streptavidin, and the biotin-labeled luminescent polymer is bound to the antibody to form a complex, while "indirect binding" refers, for example, to a case in which an, antibody (the so-called second antibody) that specifically recognizes another antibody that specifically recognizes an antigen, which is the target substance, is labeled by avidin or streptavidin, and the biotin-labeled luminescent polymer is bound to the second antibody. However, the avidin or streptavidin labeling of an antibody can also be performed via biotin, for instance, and there are more detailed configurations, so the above description is not meant to be comprehensive, and basically any means can be employed as long as it allows a complex of the target substance and a biotin-labeled luminescent polymer to be formed by some means with specificity.

The complex obtained in this manner can be detected simply and at high sensitivity by using an optical procedure suited to the luminescent characteristics (fluorescence, chemiluminescence) of the luminescent polymer in the biotin-labeled luminescent polymer. Specifically, the biotin-labeled luminescent polymer of the present invention is utilizable as a luminescent signal probe on the basis of the high luminescence of its luminescent polymer. In particular, the biotin-labeled luminescent polymer of the present invention is preferably utilizable as a luminescent signal probe in the measurement of biocomponents (such as enzymes, antigens, antibodies, receptors, nucleic acids (DNA, cDNA, RNA), and so forth) of various kinds of organism, such as microbes, plants, and animals including humans. The biotin-labeled luminescent polymer of the present invention is effectively utilizable as a luminescent signal probe in variety of applications, such as the detection of specific genes by solid phase hybridization of a microarray (DNA chip) or the like, the detection of intracellular DNA or RNA by microscope image detection, or the detection of bands in DNA sequencing. Consequently, the present invention provides the application of the biotin-labeled luminescent polymer of the present invention as a luminescent signal probe.

In this Specification, the terms "detection" and "measurement" include both the quantitative and qualitative sense, and should be interpreted in the broadest definition, irrespective of any specific means or objective, such as measurement or testing for diagnosis or image analysis. Also, the above-mentioned "measurement of biocomponents of various organisms" and other such phrases are defined in a broad sense, and the term "bioassay" is used in this specification to convey this concept.

The luminescent signal probe of the present invention either is fluorescent itself or emits light by undergoing some treatment (such as oxidation) (called chemiluminescence), depending on the type of luminescent polymer used therein. Thus, the luminescent signal probe of the present invention can be a fluorescent signal probe when the luminescent polymer is a fluorescent polymer, and can be a chemiluminescent signal probe when the luminescent polymer is a chemiluminescent polymer.

Specific examples of the detection means of this luminescent signal probe are as follows. When the luminescent signal probe is a fluorescent signal probe, a complex of the fluorescent signal probe and the target substance to be measured is irradiated with fluorescent light of a suitable excitation wavelength, and the resulting fluorescent intensity is detected and measured with a dedicated fluorometer or other photometer. When the luminescent signal probe is a chemiluminescent signal probe, a complex of the chemiluminescent signal probe and the target substance to be measured is subjected to a chemiluminescent reaction under oxidative reaction conditions suited to the respective luminescent matrices, and the resulting chemiluminescent intensity is detected and measured with a dedicated luminometer or other photometer.

FIG. 1 is an example in which the target substance is DNA, and schematically illustrates the principle behind a method for detecting a target substance (hereinafter also referred to as target DNA) using the biotin-labeled luminescent polymer of the present invention as a luminescent signal probe.

As shown in FIG. 1, when the target DNA is directly or indirectly labeled ahead of time with avidin or streptavidin, a complex of target DNA and a luminescent polymer via the biotin can be formed, in which the biotin being in the luminescent signal probe (biotin-labeled luminescent polymer) of the present invention, and the target DNA can be detected and measured using the luminescence of the luminescent polymer as an index.

Examples of how the target DNA Is labeled with avidin or streptavidin here include a method in which the target DNA is prelabeled with biotin, and then avidin or streptavidin is bound thereto as shown in FIG. 1, a method in which avidin or streptavidin is bound directly to the target DNA, and a method in which DNA fragments that can be hybridized to the target DNA are labeled with biotin ahead of time, and the resulting biotin-labeled DNA fragments are hybridized to the target DNA and avidin or streptavidin is bound thereto.

When the target DNA is to be specifically detected and measured from biocomponents in which various kinds of DNA are admixed, for example, a substance having affinity to the target DNA, such as DNA fragments that can be hybridized to the target DNA, are first fixed on a solid phase (a support), the target DNA is trapped thereon, and then a complex of the target DNA and a luminescent polymer is formed by one of the above methods.

Further, as shown in FIG. 1, when the luminescent signal probe (biotin-labeled luminescent polymer) is labeled with two or more biotins, many luminescent signal probes (biotin-labeled luminescent polymers) can be bound to a single molecule of the target DNA cooperatively in a network structure through binding with avidin or streptavidin. With a luminescent signal probe (biotin-labeled luminescent polymer) thus labeled with two or more biotins, the luminescent intensity imparted to each molecule of target DNA can be amplified, which allows this DNA to be detected at high sensitivity. In this sense, the luminescent signal probe of the present invention itself amplifies luminescence by binding cooperatively and forming in a network structure, and therefore can be defined as a luminescent amplification probe and, as a result, as a high-sensitivity luminescent signal probe. Therefore, a bioassay involving the luminescent signal probe of the present invention that has been labeled with two ore more biotins (discussed below) can also be defined as a luminescent amplification method.

(2-2) Luminescent Reagent and Luminescent Reagent Kit

The present invention also provides the use application of the above-mentioned biotin-labeled luminescent polymer of the present invention as a luminescent reagent. The luminescent reagent of the present invention comprises at least the above-mentioned biotin-labeled luminescent polymer of the present invention, and can be used to advantage in bioassay. The biotin-labeled luminescent polymer in this luminescent reagent is a luminescent signal probe, and could also be a luminescent amplification probe. The luminescent reagent of the present invention may also be such that the biotin-labeled luminescent polymer (luminescent signal probe or luminescent amplification probe) of the present invention is prebound with avidin or streptavidin to form a complex (hereinafter referred to as "biotin-labeled luminescent polymer+(strept) avidin complex"). The luminescent reagent of the present invention can be provided in any desired form, such as a solution or a powder or other solid.

A luminescent reagent kit comprising one or more of the following ① to ③ depending on the object, in addition to the above-mentioned luminescent reagent comprising the biotin-labeled luminescent polymer as an essential component (such as (a) a biotin-labeled luminescent polymer and (b) a biotin-labeled luminescent polymer+(strept)avidin complex) (number ④ below), can also be used for the measurement of a target substance in bioassay or the like.
① An insoluble carrier to which is bound a substance capable of specifically binding the target substance
② A biotin-labeled substance capable of specifically binding to the target substance
③ Avidin or streptavidin
④ a luminescent reagent ((a) a biotin-labeled luminescent polymer and (b) a biotin-labeled luminescent polymer+ (strept)avidin complex)

When the luminescent reagent (④) is (a) a biotin-labeled luminescent polymer (luminescent signal probe), the preferred luminescent reagent kit of the present invention comprises at least the above ② to ④ as constituent components, and even more preferably comprises all of the above ① to ④ as constituent components. When the luminescent reagent is (b) a biotin-labeled luminescent polymer+(strept)avidin complex, the preferred luminescent reagent kit of the present invention comprises at least the above ② and ④ as constituent components, and preferably comprises the above ①, ②, and ④ as constituent components.

Including component ① along with components ② to ④ as constituent components of the luminescent reagent kit allows the biotin-labeled substance of ② above to be bound to the target substance that has been fixed by binding the target substance on an insoluble carrier.

Examples of the "substance capable of specifically binding the target substance" referred to in ① above include substances having specific affinity with the target substance, such as an antigen (or antibody) to an antibody (or antigen) that is the target substance, or complementary nucleic acid fragments capable of hybridizing with that nucleic acid that is the target substance. The "insoluble carrier" referred to in ① is used as a support (solid phase) for fixing the target substance, and any of the various supports (solid phases) in common use in this field can be employed. Examples include a variety of materials, such as glass, cellulose, Sephadex, Sepharose, polystyrene, filter paper, carboxymethyl cellulose, ion exchange resin, dextran, plastic film, plastic tubing, nylon, silk, polyamine-methyl vinyl ether-maleic acid copolymer, amino acid copolymer, ethylene-malein copolymer, and other such materials in the form of sticks, beads, plates (including microplates), test tubes, and so forth.

The " . . . substance capable of specifically binding to the target substance" referred to in ② above encompasses both substances that bind directly to the target substance, and substances that bind indirectly. Just as discussed above, specific examples of substances that bind directly to the target substance include substances having specific affinity with the target substance, such as an antigen (or antibody) to an antibody (or antigen) that is the target substance, or complementary nucleic acid fragments capable of hybridizing with that nucleic acid that is the target substance. Examples of substances that bind indirectly to the target substance include so-called second antibodies, and antibodies to double stranded DNA.

The various above-mentioned constituent components (① to ④) can be used in combination with one or more substances selected appropriately from adjust pH, such as phosphoric acid, a Tris buffer, and Good's buffer; substances known to have the effect of stabilizing the components, such as sodium chloride and other salts, protein components (such as albumin), and sugar components (such as sucrose); solubilizing agents, such as surfactants; substances known to have the effect of suppressing non-specific reactions, such as surfactants, gelatin, or casein; antiseptics such as sodium azide or Proclin (trade name of Supelco); and any other substances commonly known to be useful in detection and measurement.

The biotin-labeled luminescent polymer (luminescent signal probe) contained as an essential component in the luminescent reagent may itself be water-soluble, but at least should be one that will not insolubilize (precipitate or settle) in the measurement reaction system used for the bioassay. More specifically, it should exhibit a solubility of at least 0.5 mg/mL in the reaction solution of the measurement system.

(2-3) Bioassay Method

The present invention further provides a bioassay method with the use of the biotin-labeled luminescent polymer of the present invention. In this bioassay method, the biotin-labeled luminescent polymer of the present invention can be used effectively as a luminescent signal probe or a luminescent amplification probe.

The bioassay method of the present invention involves measuring a target substance by detecting luminescence from a complex formed by this target substance and a biotin-labeled luminescent polymer. In specific terms, the bioassay method of the present invention comprises a step of forming a complex of the target substance and the biotin-labeled luminescent polymer directly or indirectly via avidin or streptavidin, and assaying the complex thus formed by detecting luminescence from the complex.

As discussed above, the target substance to be assayed can be selected from a variety of biological components from various kinds of organism, such as enzymes, antibodies, antigens, receptors, and other proteins, and nucleic acids (cDNA, DNA, RNA).

Specifically, the bioassay method of the present invention can be performed by a procedure comprising the following steps (i), (ii), and (iii):
(i) attaching biotin to the target substance;
(ii) complexing the biotin-labeled target substance obtained in the step (i), avidin or streptavidin, and the above-mentioned biotin-labeled luminescent polymer; and
(iii) assaying the complex obtained in step (ii) comprising the biotin-labeled target substance, the avidin or streptavidin, and the above-mentioned biotin-labeled luminescent polymer by detecting chemiluminescence or fluorescence from the complex.

The target substance to be assayed may be fixed to an insoluble carrier (support) prior to step (i).

The bioassay method of the present invention allows the target substance to be assayed at high sensitivity on the basis of using a biotin-labeled luminescent polymer having high luminescent intensity as a luminescent signal probe. Also, the biotin-labeled luminescent polymer used for this luminescent signal probe is preferably a water-soluble compound (polysaccharides, polyamino acids, polypeptides, and other such modified compounds) with high affinity to biocomponents. Accordingly, the bioassay method of the present invention tends not to be limited by the solubility of the reagent, and can be utilized in the assay of biocomponents.

In the case of a bioassay method using a biotin-labeled luminescent polymer labeled with two or more biotins that binds to the biotin-labeled target substance, each of the biotin-labeled luminescent polymers (luminescent signal probe) is bound cooperatively through binding with avidin or streptavidin to form a complex comprising of two or more biotin-labeled luminescent polymers in a network structure, by the reaction in step (ii). Therefore, according to this bioassay method using the biotin-labeled luminescent polymers whose luminescent intensity has been amplified by the formation of the above-mentioned complex as a luminescent signal probe, it is possible to measure a biotin-labeled target substance at higher sensitivity. In this respect the bioassay method of the present invention can be defined as a luminescent amplification method. Thus, the bioassay method of the present invention can be effectively utilized in the measurement of minute amounts of biocomponents, particularly nucleic acids, antigens, antibodies, and so forth.

EXAMPLES

Examples will now be given to describe the present invention in further detail, but the present invention is not limited to or by these examples.

Reference Example 1

Synthesis of Cyanoisoindoles (1) 4-(2'-cyanoisoindolyl)phenylisothiocyanate [N-(4-isothiocyanatophenyl)-1-cyanoisoindole](i) 4-(2'-cyanoisoindolyl)aniline [N-(4-aminophenyl)-1-cyanoisoindole]

A mixture of 536 mg (4 mmol) of o-phthalaldehyde, 600 mg (4 mmol) of p-aminoacetanilide, and 260 mg (4 mmol) of potassium cyanide was stirred for 90 minutes at room temperature (25 to 28° C.) in a mixed solvent of 1 mL water and 15 mL methanol. The insoluble product (compound I) thus produced was removed by filtration and washed with 5 mL of cold methanol. This compound I was suspended in 60 mL of ethanol and refluxed for 10 hours in the presence of 30 mL of 1 M hydrochloric acid. The reaction mixture was concentrated in vacuo to obtain the titled 4-(2'-cyanoisoindolyl) aniline expressed by the following formula in the form of a colorless, bright, crystalline powder (compound II, approximately 100 mg).

[Thirty-Fifth Chemical Formula]

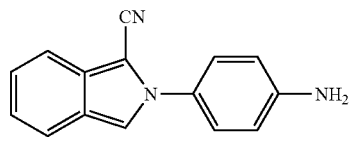

(ii) 4-(2'-cyanoisoindolyl)phenylisothiocyanate [N-(4-isothiocyanatophenyl)-1-cyanolsolndole]

84 mg (0.36 mmol) of 4-(2'-cyanoisoindolyl)aniline was suspended in 40 mL of a mixture of benzene and tetrahydrofuran (1:1, v/v) and refluxed for 1 hour in the presence of 65 mg (0.64 mmol) of triethylamine and 40 mg (0.35 mmol) of thiophosgene. The reaction mixture was concentrated under a vacuum, and then the residue was recrystallized with acetonitrile to obtain 37 mg of the titled 4-(2'-cyanoisoindolyl) phenylisothiocyanate expressed by the following formula in the form of a colorless needle crystal.

[Thirty-Sixth Chemical Formula]

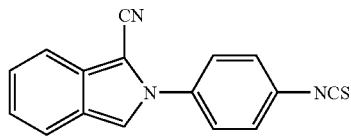

m.p. (uncorrected): 172° C.
EI-MS (m/z): 275 (M)
Elemental analysis:
Calculated values: C, 69.82; H, 3.27; N, 15.27%
Measured values: C, 69.67; H, 3.29; N, 15.22%
$^1$H-NMR (δ, ppm): 7.14-7.75 (9H, multiplet, aromatic protons)

(2) (2'-cyanoisoindolyl)ethylisothiocyanate [N-(2-isothiocyanatoethyl)-1-cyanoisoindole] (i) (2'-cyanoisoindolyl)ethylamine [N-(2-aminoethyl)-1-cyanoisoindole]

The titled (2'-cyanoisoindolyl)ethylamine expressed by the following formula was obtained in the same manner as in (1)(1) above, except that N-acetylethylenediamine was used instead of the p-aminoacetanilide.

[Thirty-Seventh Chemical Formula]

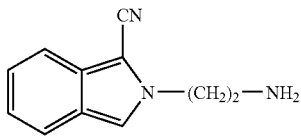

(ii) (2'-cyanoisoindolyl)ethylisothiocyanate [N-(2-isothiocyanatoethyl)-1-cyanoisoindole]

The titled (2'-cyanoisoindolyl)ethylisothiocyanate expressed by the following formula was obtained in the same manner as in (1)(ii) above, except that (2'-cyanoisoindolyl) ethylamine was used instead of the 4-(2-cyanoisoindolyl) aniline.

[Thirty-Eighth Chemical Formula]

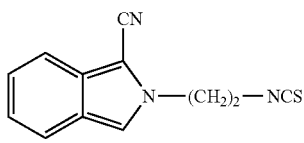

m.p. (uncorrected): 113° C.
EI-MS (m/z): 227 (M+)
Elemental analysis:
Calculated values: C, 62.62; H, 4.08; N, 18.26%
Measured values: C, 62.76; H, 4.08; N, 17.75%

Example 1

Water-Soluble Luminescent Polymer (Polyamino Acid)

(1-1) Polylysine to which 1.6 4-(2'-cyanoisoindolyl)phenyl-isothiocyanate Molecules are Attached (Luminescent Polymer (1))

56 mg (54 µmol) of polylysine (a 5 oligomer of lysine; poly(L-Lys)$_5$.5HBr; average molecular weight 1045) was dissolved in 2 mL of water, 30 mL of pyridine and 79 mg (287 µmol) of 4-(2'-cyanoisoindolyl)phenylisothiocyanate were added to the solution, and the mixture was heated for 30 minutes at 50° C., after which the solvent was distilled away from the reaction solution under reduced pressure. The residue was dissolved in 50 mL of a mixture of acetonitrile and water (45:55, % v/v), and the solution was injected into a preparative gel column (Sephadex LH 20) and separated with an eluent consisting of acetonitrile and water (45:55, % v/v). The fluorescent peak originating in the 4-(2'-cyanoisoindolyl) phenyl group (4-[2-(1'-cyanoisoindolyl)]phenyl group) expressed by the following formula was traced, and a fraction containing a high-molecular compound to which the 4-(2'-cyanoisoindolyl)phenyl groups were bound was separated.

[Thirty-Ninth Chemical Formula]

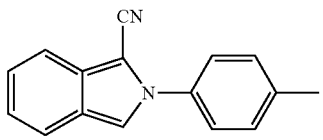

The acetonitrile in the fraction was distilled away under reduced pressure, and this product was freeze-dried to obtain 53 mg of polylysine to which 4-(2'-cyanoisoindolyl)-phenyl groups were attached (luminescent polymer (1)).

The luminescent polymer thus obtained was measured by $^1$H-NMR (d6-DMSO solvent; 500 MHz), in which 40H for the alkylene groups of the lysine was observed at δ 1.37-4.26, and 13H for the aromatic rings of the 4-(2'-cyanoisoindolyl) phenyl groups was observed at δ 7.2-7.8. The calculated average for the number of 4-(2'-cyanoisoindolyl)phenyl groups attached to each molecule of polylysine by the thiocarbamoyl bond in the produced compound was approximately 1.6.

(1-2) Biotin Labeling (Biotin-Labeled Luminescent Polymer (6))

Biotin was attached to the amino groups of the polylysine (1) obtained above, to which 4-(2'-cyanoisoindolyl)phenyl groups were attached, using an EZ-Link Sulfo-NHS-Biotinylation Kit (from Pierce) according to the instruction manual thereof. In specific terms, 10 mg of the luminescent polymer (1) obtained above was dissolved in 1 mL of PBS, to which 40 mg of sulfo-N-hydroxysuccinimide-biotin was added and dissolved, and this solution was allowed to stand for 30 minutes at room temperature. The obtained solution was applied to a desalting column supplied with the Kit. The fluorescent peak was traced, and a fraction containing the biotin-labeled luminescent polymer (6) was obtained.

(2-1) Polylysine to which Eight 4-(2'-cyanoisoindolyl)phenyl-isothiocyanate Molecules are Bound (Luminescent Polymer (2))

49 mg (9 µmol) of polylysine (a 42 oligomer of lysine; poly(L-Lys)$_{42}$.42HBr; average molecular weight 8800) was dissolved in 0.8 mL of water, 6 mL of pyridine and 20 mg (73 µmol) of 4-(2'-cyanoisoindolyl)phenylisothiocyanate were added to the solution, and the mixture was heated for 30 minutes at 50° C., after which the solvent was distilled away from the reaction solution under reduced pressure. The residue was dissolved in 35 mL of a mixture of acetonitrile and water (45:55, % v/v), and this solution was injected into a preparative gel column (Sephadex LH 20) and separated with an eluent consisting of acetonitrile and water (45:55, % v/v). The fluorescent peak originating in the 4-(2'-cyanoisoindolyl) phenyl groups was traced, and a fraction containing a high-molecular compound to which the 4-(2'-cyanoisoindolyl) phenyl groups were bound was separated. The acetonitrile in the fraction was distilled away under reduced pressure, and this product was freeze dried to obtain 49 mg of polylysine to which 4-(2'-cyanoisoindolyl)phenyl groups were attached (luminescent polymer (2)).

The luminescent polymer thus obtained was measured by $^1$H-NMR (d6-DMSO solvent; 500 MHz), in which 336H for the alkylene groups of the lysine was observed at δ 1.38-4.2, and 64H for the aromatic rings of the 4-(2'-cyanoisoindolyl) phenyl groups was observed at δ 7.2-7.8. The calculated average for the number of 4-(2'-cyanoisoindolyl)phenyl groups attached to each molecule of polylysine by the thiocarbamoyl bond in the produced compound was found to be approximately 8.

(2-2) Biotin Labeling (Biotin-Labeled Luminescent Polymer (7))

Biotin was bound to the amino groups of the polylysine (2) obtained above, to which 4-(2'-cyanoisoindolyl)phenyl groups were bound, using an EZ-Link Sulfo-NHS-Biotinylation Kit (from Pierce) according to the instruction manual thereof. In specific terms, 10 mg of the luminescent polymer (2) obtained above was dissolved in 1 mL of PBS, to which 40 mg of sulfo-N-hydroxysuccinimide-biotin was added and dissolved, and this solution was allowed to stand for 30 minutes at room temperature. The obtained solution was applied to a desalting column supplied with the Kit. The fluorescent peak was traced, and a fraction containing the biotin-labeled luminescent polymer (7) was obtained.

Example 2

Water-Soluble Luminescent Polymer (Polysaccharide, Part 1)

Dextran to which Thirty 4-(2'-cyanoisoindolyl)aniline Molecules are Attached (Luminescent Polymer (3))

470 mg (28 µmol) of dextran (average molecular weight 16,800: an average of 104 glucoses are polymerized) was dissolved in 10 mL of water, 381 mg (1.8 mmol) of sodium periodate was added to the solution, and the mixture was stirred for 40 minutes at room temperature. This reaction oxidized approximately 30% of the glucoses in the dextran. 15 mL of water was added to this reaction solution, and the obtained solution was fallen in drops into 250 mL of methanol. The precipitated oxidized dextran was recovered by filtration and dried under reduced pressure (yield of the oxidized dextran: 410 mg). 50 mg thereof was dissolved in 6 mL of ethylene glycol, this solution was mixed with a solution obtained by dissolving 98 mg (420 µmol) of 4-(2'-cyanoisoindolyl)aniline in 3 mL of tetrahydrofuran, and this mixture was stirred for 24 hours at room temperature. This reaction solution was fallen in drops into 100 mL of methanol. The precipitate thus produced was collected, suspended again in 400 mL of methanol, and stirred for 15 hours at room temperature, which gave 54 mg of dextran to which 4-(2'-cyanoisoindolyl)-phenyl groups were attached (luminescent polymer (3)). A portion of the obtained luminescent polymer was applied to high-performance liquid chromatography (using a gel column containing TSK gel G2000SW, and using an aqueous solution of 0.1% (v/v) trifluoroacetic acid containing 15% (v/v) acetonitrile as the eluent), which confirmed that the free 4-(2'-cyanoisoindolyl)aniline had not been adsorbed by the luminescent polymer.

The luminescent polymer obtained above was subjected to an elemental analysis (measured values: C, 51.17%; H, 5.67%; N, 5.12%; calculated values: C, 51.17%; H, 5.41%; N, 5.12%), which revealed that a calculated average of approximately thirty 4-(2'-cyanoisoindolyl)phenyl groups had been attached by the dehydration/condensation reaction of amino groups thereof to a molecule of dextran consisting of polymerized 104 glucoses on average.

Example 3

Water-Soluble Luminescent Polymer
(Polysaccharide, Part 2)

Dextran to which 300 Luminol Molecules are Attached (Luminescent Polymer (4))

324 mg (1.9 µmol) of dextran (average molecular weight 174,000; an average of 1074 glucoses are polymerized) was dissolved in 10 mL of water, 283 mg (1.3 mmol) of sodium periodate was added to the solution, and the mixture was reacted for 30 minutes at room temperature. This reaction oxidized approximately 33% of the glucoses in the dextran. 500 mL of this reaction solution was fallen in drops into methanol, and the precipitate of oxidized dextran was recovered by filtration, and dried under reduced pressure (a yield of the oxidized dextran: 260 mg). 100 mg of this oxidized dextran was dissolved in 10 mL of dimethyl sulfoxide at 60° C., after which 95 mg (540 µm) of luminol and 5 mL of acetic acid were admixed, and this mixture was stirred for 24 hours at 60° C. This reaction solution was fallen in drops into 500 mL of methanol. The precipitate thus produced was recovered by filtration and dried under reduced pressure (a yield of the precipitate: 56 mg). 30 mg of this precipitate was dissolved in 20 mL of ethylene glycol at 60° C., after which 10 mg (264 µmol) of sodium borohydride was gradually added, and the mixture was allowed to stand for 2.5 hours. The reaction solution was fallen in drops into 300 mL of acetone to precipitate the reduced product. The precipitate was recovered by filtration, suspended in 500 mL of methanol, and stirred for 15 hours at room temperature, which gave 28 mg of dextran to which luminol was bound (luminescent polymer). A portion of the luminescent polymer was applied to high-performance liquid chromatography (using a gel column containing TSK gel G2000SW, and using an aqueous solution of 0.1% (v/v) trifluoroacetic acid as the eluent), which confirmed that the free luminol had not been adsorbed by the luminescent polymer.

The luminescent polymer obtained above was subjected to an elemental analysis (measured values: C, 43.93%; H, 5.12%; N, 5.47%; calculated values: C, 44.33%; H, 4.96%; N, 5.47%), which revealed that a calculated average of approximately 300 luminol molecules had been attached to a molecule of dextran consisting of polymerized 1074 glucoses on average, by the dehydration/condensation and reduction reactions of the amino groups in the luminol and aldehyde groups in the dextran.

Example 4

Biotin-Labeled Luminescent Polymer

Water-Soluble Luminescent Polymer to which 300 Luminol Molecules and 15 Biotin Molecules are Attached (Biotin-Labeled Luminescent Polymer (5))

100 mg of the oxidized dextran synthesized in Example 3 above was dissolved in 10 mL of dimethyl sulfoxide at 60° C., after which 95 mg (540 µmol) of luminol and 5 mL of acetic acid were added and stirred for 24 hours at 60° C., and then 10 mg (27 µmol) of biotinamidopentamethylene hydrazide was added and stirred for 2.5 hours at room temperature.

This reaction solution was fallen in drops into 500 mL of methanol. The precipitate thus produced was dried under reduced pressure (a yield of the precipitate: 59 mg). 30 mg of this dry precipitate was dissolved in 20 mL of ethylene glycol at 60° C., after which 10 mg of sodium borohydride was gradually added, and the mixture was allowed to stand for 2.5 hours at room temperature. This solution was fallen in drops into 300 mL of acetone. The precipitate thus produced was recovered by filtration and suspended in 500 mL of methanol, and the mixture was stirred for 2 hours at room temperature, after which the solution was again filtered to obtain 21 mg of dextran to which luminol and biotin were bound (biotin-labeled luminescent polymer). A portion of the polymer was applied to high-performance liquid chromatography (using a gel column containing TSK gel G2000SW, and using an aqueous solution of 0.1% trifluoroacetic acid as the eluent), which confirmed that the free luminol had not been adsorbed by the biotin-labeled luminescent polymer.

The biotin-labeled luminescent polymer obtained above was subjected to an elemental analysis (measured values: C, 44.12%; H, 6.18%; N, 5.76%; calculated values: C, 44.30%; H, 6.24%; N: 5.76%), which revealed this polymer to be a water-soluble biotin-labeled luminescent polymer in which a calculated average of approximately 300 luminol molecules had been attached to a molecule of dextran consisting of polymerized 1074 glucoses on average, by the dehydration/condensation and reduction reactions of an amino group in luminol and an aldehyde group in glucose ring-opened by oxidation, and in which approximately 15 biotin molecules were attached to a molecule of dextran, via the aldehyde groups of glucoses ring-opened by oxidation in the dextran.

Example 5

Biotin-Labeled Luminescent Polymer (8)

Water-Soluble Biotin-Labeled Luminescent Polymer to which Thirty 4-(2'-cyanoisoindolyl)aniline Molecules and Biotin Molecules are Attached (Biotin-Labeled Luminescent Polymer (8))

50 mg of the oxidized dextran manufactured in Example 2 above was dissolved in 6 mL of ethylene glycol, this solution was mixed with a solution obtained by dissolving 98 mg (420 µmol) of 4-(2'-cyanoisoindolyl)aniline in 3 mL of tetrahydrofuran, and this mixture was stirred for 24 hours at room temperature. Then, 8 mg (22 µmol) of biotinamidohexanoic acid hydrazide (from Sigma) was added and stirred for 2.5 hours at room temperature. This reaction solution was fallen in drops into to 500 mL of methanol. The precipitate thus produced was dried under reduced pressure. 30 mg of this dry precipitate was dissolved in 20 mL of ethylene glycol at 60° C., after which 10 mg of sodium borohydride was gradually added, and the mixture was allowed to stand for 2.5 hours. This solution was fallen in drops into to 300 mL of acetone. The precipitate thus produced was recovered by filtration and suspended in 500 mL of methanol, and the mixture was stirred for 2 hours at room temperature, after which the solution was again filtered to obtain a polymer, that is dextran to which 4-(2'-cyanoisoindolyl)phenyl group and biotin was attached (biotin-labeled luminescent polymer (8)).

Example 6

Biotin-Labeled Luminescent Polymer

Water-Soluble Luminescent Polymer to which 1900 Luminol Molecules and 400 Biotin Molecules are Attached (Biotin-Labeled Luminescent Polymer (9))

60 mg of dextran (average molecular weight: 2,000,000; an average of 12,000 glucoses are polymerized) was dissolved in 30 mL of water, 47 mg of sodium periodate was added, and the mixture was reacted for 2 hours at room temperature. This reaction solution was fallen in drops into 300 mL of methanol, and the precipitate of oxidized dextran was recovered by filtration, dissolved again in 30 mL of water, and reprecipitated with 300 mL of methanol. The oxidized dextran was recovered by filtration and all of it was dissolved in 12 mL of dimethyl sulfoxide, after which 4 mL of glacial acetic acid was added, and then 79 mg of isoluminol and 3.2 mg of biotinamidohexanoic acid hydrazide (from Sigma) were added and stirred for 60 hours at room temperature. This reaction solution was fallen in drops into 160 mL of methanol. The precipitate thus produced was dried under reduced pressure (a yield of the precipitate: 52 mg). 52 mg of this dry precipitate was dissolved in 20 mL of ethylene glycol and 15 mL of dimethyl sulfoxide at 60° C., after which 442 mg of sodium borohydride was gradually added at 4° C., and the mixture was allowed to stand for 9 hours. This solution was fallen in drops into 350 mL of acetone. The precipitate thus produced was recovered by filtration to obtain 75 mg of dextran to which isoluminol and biotin were attached (biotin-labeled luminescent polymer).

The polymer obtained above was subjected to an elemental analysis (measured values: C, 36.56%; H, 5.48%; N, 3.55%; S, 0.40%; calculated values: C, 36.05%; H, 7.32%; N, 3.53%; S: 0.42%), which revealed this compound to be a water-soluble biotin-labeled luminescent polymer in which a calculated average of approximately 1900 isoluminol molecules were attached to a molecule of dextran consisting of polymerized 12,000 glucoses on average, by the dehydration/condensation reaction and reduction reaction of an amino group in isoluminol molecule and an aldehyde group of the glucose ring-opened by oxidation, and in which approximately 400 biotin molecules were attached to a molecule of the dextran, via the aldehyde groups of the glucoses ring-opened by oxidation in the dextran.

Example 7

Evaluation of Chemiluminescence

The polymers (1) to (5) prepared in Examples 1 to 4 were measured for chemiluminescent intensity by the following procedure.
[Measurement Procedure]
Each of the polymers (1) to (3) was dissolved in water, 5 µL of this solution was put in a test tube, to which were added 100 µL of 0.3 M sodium borate buffer (pH 11), 100 µL of acetonitrile, and 100 µL of 4.9 M $H_2O_2$ aqueous solution containing 50% (v/v) acetonitrile, in that order, and the luminescent intensity (photon count) was measured over 10 minutes with a luminometer (model BLR-201 made by Aloka). Polymers (4) and (5) were each similarly dissolved in water, 30 µL of the solution was put in a test tube, 100 µL of a 0.1 M sodium carbonate aqueous solution, 20 µL of a 0.1 M $H_2O_2$ aqueous solution, and 50 µL of acetonitrile were added in that order, and the luminescent intensity (photon count) was measured over 10 minutes in the same manner as above. For the sake of comparison, the luminescent intensity (photon count) was similarly measured for the chemiluminescent substances, 4-(2'-cyanoisoindolyl)aniline and luminol, used themselves in the synthesis of the luminescent polymer.
[Results]
Table 1 shows the luminescent intensity obtained for each compound.

TABLE 1

Comparison of chemiluminescent intensity of various compounds

| Compound (1 picomole/test tube) | Number of low-molecular weight luminescent substances contained in each polymer molecule | Chemiluminescent intensity (photon count over 10 minutes) |
|---|---|---|
| Polymer (1) | 1.6 | 148 |
| Polymer (2) | 8 | 1,000 |
| Polymer (3) | 30 | 6,510 |
| Polymer (4) | 300 | 8,780,000 |
| Polymer (5) | 300 | 10,200,000 |
| *4-(2'-cyanoisoindolyl)aniline | | 30 |
| *Luminol | | 2,540,000 |

As shown by the table, polymers (1) to (3), to which 4-(2'-cyanoisoindolyl)phenyl groups were attached, exhibited markedly higher luminescent intensity than 4-(2'-cyanoisoindolyl)aniline with an equivalent number of 4-(2'-cyanoisoindolyl)phenyl groups, and it can also be seen that the greater was the polymerization, the more the luminescent intensity tended to increase.

With polymers (4) and (5), to which approximately 300 luminol molecules (calculated) were attached, the increase in luminescent intensity was less than expected, but the intensity was still higher than that with luminol alone (approximately 4 times higher).

It is not clear why the increase in luminescent intensity was less than expected, but there has been a report that modification of an amino group of luminol with an alkyl group or a phenyl group reduces the luminescent intensity to about one-hundredth the luminescent intensity of luminol, based on chemiluminescent quantum yield (C. Dodeiigne et al., Talanta, 51, 415-439 (2000)), so the same phenomenon might be occurring here.

The luminescent intensity of polymers (4) and (5) seems to be about 30,000, calculated as the luminescent intensity per a luminol molecule attached to the polymers. This is equivalent to approximately one-eighty-fifth the chemiluminescent quantum yield of luminol alone. Given this, it would seem that polymers (4) and (5) have chemiluminescent intensity that is substantially proportional to the degree of polymerization of the luminescent substance (luminol) attached to each.

As shown by Table 1, the luminescent intensity of polymer (5), to which biotin was attached, was higher than that of polymer (4). This result suggests that a polymer with stronger luminescence can be obtained by polymerizing a luminescent substance with a high luminescent quantum yield to a larger polymer. Polymer (5) has the highest intensity per molecule of any chemiluminescent compound known at this time.

Example 8

Evaluation of Fluorescence

The polymers (1) to (3) prepared in Examples 1 and 2 were measured for fluorescent intensity by the following procedure.
[Measurement Procedure]
Each of the polymers (1) to (3) was dissolved in water, 1.0 mL of this solution was put into a quartz cell for fluorescent measurement, and the spectrum was measured with a spectrofluorophotometer. The relative fluorescent intensity was then determined at the excitation maximum wavelength and fluorescence maximum wavelength (uncorrected).
[Results]
Table 2 shows the fluorescent intensity of each compound.

TABLE 2

Comparison of fluorescent intensity of various compounds

| Compound (1 nanomole/mL) | Number of low-molecular weight luminescent substances contained in each polymer molecule | Relative fluorescent intensity | (Excitation wavelegth/ fluorescence wavelength |
|---|---|---|---|
| Polymer (1) | 1.6 | 29 | (345 nm/415 nm) |
| Polymer (2) | 8 | 74 | (345 nm/415 nm) |
| Polymer (3) | 30 | 25,000 | (355 nm/460 nm) |
| *4-(2'-cyanoisoindolyl)aniline | | 2,600 | (340 nm/460 nm) |

As shown by the table, polymers (1) and (2), to which 4-(2'-cyanoisoindolyl)phenylisothiocyanate groups were attached, increased in fluorescence according to the how many of these groups were attached. The fluorescent intensity of 4-(2'-cyanoisoindolyl)phenylisothiocarbamoyl is about one-hundredth that of the 4-(2'-cyanoisoindolyl)aniline shown in Table 2 (relative fluorescent intensity: approximately 26). This confirms that the fluorescent intensity of polymer (1) or (2), to which 4-(2'-cyanoisoindolyl)phenylisothiocyanate groups were attached, is higher than the fluorescent intensity of 4-(2'-cyanoisoindolyl)phenylisothiocarbamoyl, and that the intensity increases in proportion to the number of groups attached. The fluorescent intensity of polymer (3), to which approximately thirty 4-(2'-cyanoisoindolyl)aniline molecules were attached, was approximately 10 times higher than that of 4-(2'-cyanoisoindolyl)aniline alone.

Example 9

Utilization as a Luminescent Signal Probe

Chemiluminescent detection of target DNA was performed using the biotin-labeled luminescent polymer (5) prepared in Example 4 as a luminescent signal probe.

Specifically, sample DNA in which biotin was bound to the 5'-terminal (biotin-labeled DNA, 0.1 fmol=$1 \times 10^{-16}$ mol) was adsorbed to a nylon film, and this was reacted with streptavidin (10 fmol) and the biotin-labeled luminescent polymer (5) (100 fmol) prepared in Example 4, for 1 hour at 37° C. in a 0.1 M sodium phosphate buffer (pH 7). After the reaction, the nylon film was taken out of the reaction solution and washed in a separate petri dish with a 0.1 M sodium phosphate buffer (pH 7) and water, which removed from the film any streptavidin and the biotin-labeled luminescent polymer (5) of Example 4 that had not been bound. The resulting film was immersed for 2 seconds in a solution containing 0.05 M sodium carbonate, 0.01 M $H_2O_2$, and 25% (v/v) acetonitrile, and immediately taken by CCD camera for chemiluminescent detection (model AE-6930 Densidograph Lumino made by Atto) to detect of the biotin-labeled DNA.

[Results]
The chemiluminescent intensity obtained from the biotin-labeled luminescent polymer (5) bound via streptavidin to the sample DNA on the film was approximately 20 times greater than the chemiluminescent intensity obtained from the same amount (0.1 fmol) of biotin-labeled luminescent polymer (5) as in the sample DNA (0.1 fmol). The result may show that in the reaction system comprising the above-mentioned biotin-labeled DNA, streptavidin, and biotin-labeled luminescent polymer, many of the biotin-labeled luminescent polymers (5) bound via the streptavidin to the biotin-labeled DNA are bound in a chain to other biotin-labeled luminescent polymers (5).

Consequently, it should be possible in this example to bind the biotin-labeled luminescent polymer (5) with another biotin-labeled luminescent polymer (5) via streptavidin in a chain reaction, and to obtain even higher detection sensitivity, by selecting the optimal conditions for the binding reaction between the biotin-labeled luminescent polymer (5) and the streptavidin, and then adjusting the reaction to meet these conditions. Also, the biotin-labeled luminescent polymer (5) shown in Table 1 exhibits intense luminescence all by itself, but the results of this example reveal that detection at extremely high sensitivity can be achieved by utilizing the biotin-labeled luminescent polymer (5) as a luminescent signal probe.

This detection method in which this biotin-labeled luminescent polymer (5) is used as a luminescent signal probe is also very simple, allowing the maximum quantity of light to be measured in an extremely short detection time (5 minutes or less).

Example 10

Utilization as a Luminescent Signal Probe (Part 2)

Chemiluminescent detection was performed in immunological measurement by using the biotin-labeled luminescent polymer (9) prepared in Example 6 as a luminescent signal probe.

[When the Luminescent Signal Probe is Used Just Once]

(i) Anti-C reactive protein (CRP) monoclonal antibodies were fixed to a microtiter plate for luminescent detection (Miorolite I made by Dynatech) according to a standard method, after which blocking was performed with Block Ace (made by Dainippon Pharmaceutical Co., LTD) to produce a sensitization plate (measurement plate) with anti-CRP antibody for trapping CRP ("anti-CRP antibody for trapping").

(ii) Genetic recombinant CRP (rCRP made by Oriental Yeast Enzyme) with a concentration of 0, 10, or 1000 pg/mL was added to the measurement plate in a proportion of 50 µL per well, and a reaction was conducted for 2 hours to trap the rCRP in the anti-CRP monoclonal antibodies (anti-CRP antibody for trapping) fixed to the above-mentioned measurement plate.

(iii) The reaction solution was removed and the plate was washed. And then, the biotin-labeled anti-CRP polyclonal antibodies were added to the plate and reacted for 1 hour to bind the biotin-labeled anti-CRP polyclonal antibodies to the rCRP trapped in the above-mentioned anti-CRP monoclonal antibodies fixed to the above-mentioned measurement plate.

(iv) The reaction solution was removed and the plate was washed. And then, the streptavidin was added to the plate and reacted for 1 hour to bind the streptavidin to the above-mentioned biotin-labeled anti-CRP polyclonal antibodies.

(v) The reaction solution was removed and the plate was washed. And then, the biotin-labeled luminescent polymer (9) was added and reacted for 1 hour to bind the biotin-labeled luminescent polymer (9) as a luminescent signal probe to the streptavidin. The result of these steps (i) to (v) was the formation of a complex constituted by the anti-rCRP monoclonal antibody for trapping, the rCRP, the biotin-labeled anti-CRP polyclonal antibody, the streptavidin, and the luminescent signal probe (biotin-labeled luminescent polymer (9)).

(vi-a) The reaction solution was removed and the plate was washed. And then, 25 µL each of two 50% (v/v) acetonitrile aqueous solutions, one containing 0.1 M sodium carbonate and the other containing 0.025 M $H_2O_2$, were added, and the luminescence was measured under conditions comprising 3 minutes integration and low gain using an ML1000 luminometer made by Dynatech.

[When the Luminescent Signal Probe is Used Twice]

Steps (i) to (v) were carried out in the same manner as when the above-mentioned luminescent signal probe was used just once.

(vi-b) The reaction solution was removed, and the plated was washed. And then, the streptavidin was again added to the plate and reacted for 1 hour to bind more streptavidin to the complex formed in steps (i) to (v).

(vii) The reaction solution was removed, and the plated was washed. And then, the polymer (9) was again added to the plate and reacted for 1 hour to bind more polymer (9) as a luminescent signal probe to the reaction product obtained in step (vi-b). This formed a complex in which more luminescent signal probe was bound via streptavidin to the complex formed in steps (i) to (v).

(viii) The reaction solution was removed and the plate was washed. And then, the same operation as in (vi-a) was performed, and measure luminescence.

The results obtained from the above luminescence measurement are given in Table 3. The numerical values in this table indicate the 3-minute integrated amount of relative luminescent intensity.

TABLE 3

| CRP concentration | When luminescent signal probe was used: | |
|---|---|---|
| (pg/mL) | Once | Twice |
| 0 | 0.231 | 0.236 |
| 10 | 0.294 | 0.470 |
| 1000 | 0.407 | 0.551 |

[Results]

When the biotin-labeled luminescent polymer (9) of the present invention was used just once as a luminescent signal probe, CRP could be measured on the order of pg/mL. When the biotin-labeled luminescent polymer (9) of the present invention was used twice as a luminescent signal probe, it was confirmed that luminescence was greater than with a single use. This is because the luminescent signal probe (biotin-labeled luminescent polymer (9)) of the present invention is such that many of the biotin in its molecules are bound with the streptavidin in the reaction mixture in a chain reaction, and the complex formed as a result binds with the CRP to be measured, via bonds with the biotin-labeled antibody-streptavidin, and this indicates that higher detection sensitivity can be obtained with the luminescent signal probe of the present invention.

INDUSTRIAL APPLICABILITY

The biotin-labeled luminescent polymer of the present invention has higher luminescent intensity per molecule according to the number of luminescent substances attached to the polymer, and therefore can be utilized as a labeling agent for detection, a luminescent signal probe, or a light source, which are used in various kinds of measurement. In particular, using a polymer of a monosaccharide or a polymer of amino acid as the said polymer allows the biotin-labeled luminescent polymer of the present invention to have affinity with biocomponents, so that said polymer can be used to advantage as a detection reagent or signal probe in the measurement of various kinds of biocomponents, that is, in bioassay. Furthermore, the biotin-labeled luminescent polymer of the present invention in an aspect in which two or more biotins are bound to each molecule can form a complex by binding cooperatively in a network structure through binding with avidin or streptavidin, which makes it possible to amplify the luminescent intensity.

Thus, because the biotin-labeled luminescent polymer of the present invention has high luminescent intensity per molecule and forms a complex in and of itself, its luminescent intensity can be amplified, so this polymer be used effectively as a labeling agent for high sensitivity detection, as a luminescent signal probe, or as a luminescent reagent, and particularly in the measurement of minute amounts of biocomponents.

The invention claimed is:

1. A water-soluble, luminescent polymer consisting of a single polymer molecule of a polyamino acid, peptide, polypeptide, protein, glycoprotein or polysaccharide with at least two biotin molecules covalently attached to said single polymer molecule, wherein the single polymer molecule consists of a plurality of constituent monomers, said monomers being monosaccharides and/or amino acids, wherein at least 8 chemiluminescent substances are directly covalently attached to the constituent monomers of the single polymer molecule and wherein the proportion of the constituent monomers covalently attached to the chemiluminescent substance is from 27.9 to 50% of the total monomers constituting the single polymer molecule.

2. The water-soluble luminescent polymer according to claim 1, wherein the chemiluminescent substance is at least one member selected from the group consisting of cyanoisoindoles, luminols, and acridinium esters.

3. The water-soluble luminescent polymer according to claim 1, wherein the single polymer molecule is a polysaccharide.

4. The water-soluble luminescent polymer according to claim 1, wherein the single polymer molecule is dextran or pullulan.

5. The water-soluble luminescent polymer according to claim 1, wherein the single polymer molecule includes a monosaccharide as a constituent monomer; at least one luminescent substance selected from the group consisting of cyanoisoindoles having a primary amino group, luminols having a primary amino group, and acridinium esters having a primary amino acid group is covalently attached through a dehydrative condensation to a ring-opened aldehyde group produced by the oxidation of the monosaccharide; and a hydrazino group of a hydrazide derivative of the biotin is covalently attached to a ring-opened aldehyde of another monosaccharide.

6. A luminescent reagent comprising the water-soluble luminescent polymer of claim 1.

7. The luminescent reagent according to claim 6, which comprises the water-soluble luminescent polymer in a state of being bound with avidin or streptavidin.

8. A luminescent reagent kit comprising:
a luminescent reagent of claim 6 and a biotin-labeled substance capable of specifically binding to a target substance.

9. The luminescent reagent kit according to claim 8, further comprising an insoluble carrier to which a substance capable of specifically binding the target substance is bound.

10. The luminescent reagent kit according to claim 8, which is a reagent kit used for bioassay.

11. The kit of claim 8, further comprising avidin or streptavidin.

12. The water-soluble luminescent polymer according to claim 1, wherein the proportion of the constituent monomers covalently attached to the chemiluminescent substance is from 30 to 50% of the total number of monomers constituting the single polymer molecule.

13. The water-soluble, luminescent polymer according to claim 1, wherein the single polymer molecule is a polylysine.

* * * * *